US011540937B2

(12) United States Patent
Hansen et al.

(10) Patent No.: US 11,540,937 B2
(45) Date of Patent: Jan. 3, 2023

(54) BASE PLATE AND SENSOR ASSEMBLY OF A MEDICAL SYSTEM HAVING A LEAKAGE SENSOR

(71) Applicant: Coloplast A/S, Humlebaek (DK)

(72) Inventors: Jais ASK Hansen, Jaegerspris (DK); Niels Hvid, Vedbaek (DK); Lars Erup Larsen, Maaloev (DK); Finn Speiermann, Virum (DK)

(73) Assignee: Coloplast A/S, Humlebaek (DK)

( * ) Notice: Subject to any disclaimer, the term of this patent is extended or adjusted under 35 U.S.C. 154(b) by 4 days.

(21) Appl. No.: 16/954,529

(22) PCT Filed: Dec. 20, 2018

(86) PCT No.: PCT/DK2018/050401
§ 371 (c)(1),
(2) Date: Jun. 17, 2020

(87) PCT Pub. No.: WO2019/120445
PCT Pub. Date: Jun. 27, 2019

(65) Prior Publication Data
US 2020/0330260 A1 Oct. 22, 2020

(51) Int. Cl.
*A61F 5/44* (2006.01)
*G16H 50/30* (2018.01)
(Continued)

(52) U.S. Cl.
CPC .......... *A61F 5/4404* (2013.01); *A61B 5/4283* (2013.01); *A61F 5/443* (2013.01);
(Continued)

(58) Field of Classification Search
CPC ................ A61F 5/445; A61F 13/00055; A61F 2013/00289; A61F 2013/008;
(Continued)

(56) References Cited

U.S. PATENT DOCUMENTS 2,327,514 A 8/1943 Fenwick
2,542,233 A 2/1951 Carroll
(Continued)

FOREIGN PATENT DOCUMENTS

CN 203786580 U 8/2014
CN 104902399 A 9/2015
(Continued)

*Primary Examiner* — Tatyana Zalukaeva
*Assistant Examiner* — Meagan Ngo
(74) *Attorney, Agent, or Firm* — Coloplast Corp., Coloplast A/S; Nick Baumann

(57) ABSTRACT

The disclosed is an ostomy system configured to detect a leakage of output between a base plate and/or a sensor assembly part of the ostomy system and a surface of a subject and a method of detecting the leakage of output. The ostomy system including the base plate and/or the sensor assembly part and a monitor device, the base plate and/or the sensor assembly part comprising (i) a first adhesive layer having a distal surface, a proximal surface, and a first plurality of openings, and (ii) an electrode assembly comprising a plurality of electrodes and a masking element between the plurality of electrodes and the first adhesive layer, the masking element having a second plurality of openings aligned with the first plurality of openings of the first adhesive layer, each of the aligned first and second plurality of openings exposes a portion of one of the plurality of electrodes to define one of a plurality of sensor points, the monitor device electrically coupled to the plurality of electrodes of the base plate and/or the sensor assembly part.

26 Claims, 16 Drawing Sheets

(51) Int. Cl.
*A61B 5/00* (2006.01)
*A61F 5/443* (2006.01)
*A61F 5/445* (2006.01)

(52) U.S. Cl.
CPC ............. *A61F 5/445* (2013.01); *G16H 50/30* (2018.01); *A61B 2562/04* (2013.01); *A61B 2562/164* (2013.01)

(58) Field of Classification Search
CPC ...... A61K 9/703; A61B 5/683; A61B 5/6802; A61B 5/6832; A61B 5/259; A61B 5/6833; A61B 5/68335; B32B 2037/268; D21H 27/001; D06N 3/0097; Y10T 428/1471; Y10T 428/1476
See application file for complete search history.

(56) References Cited

U.S. PATENT DOCUMENTS

| | | |
|---|---|---|
| 2,544,579 A | 3/1951 | Ardner |
| 3,214,502 A | 10/1965 | Schaar |
| 3,832,510 A | 8/1974 | Pfau et al. |
| 3,915,171 A | 10/1975 | Shermeta |
| 3,941,133 A | 3/1976 | Chen |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,982,742 A | 1/1991 | Claude |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,167,650 A | 12/1992 | Johnsen et al. |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,570,082 A | 10/1996 | Mahgerefteh et al. |
| 5,593,397 A | 1/1997 | La Gro |
| 5,672,163 A | 9/1997 | Ferreira et al. |
| 5,677,221 A | 10/1997 | Tseng |
| 5,704,905 A | 1/1998 | Jensen et al. |
| 5,790,036 A | 8/1998 | Fisher et al. |
| 5,800,415 A | 9/1998 | Olsen |
| 5,816,252 A | 10/1998 | Faries, Jr. et al. |
| 5,834,009 A | 11/1998 | Sawers et al. |
| 5,879,292 A | 3/1999 | Sternberg et al. |
| 6,015,399 A | 1/2000 | Mracna et al. |
| 6,025,725 A | 2/2000 | Gershenfeld et al. |
| 6,057,689 A | 5/2000 | Saadat |
| 6,103,033 A | 8/2000 | Say et al. |
| 6,135,986 A | 10/2000 | Leisner et al. |
| 6,171,289 B1 * | 1/2001 | Millot ................ A61F 5/443 604/336 |
| 6,206,864 B1 | 3/2001 | Kavanagh et al. |
| 6,407,308 B1 | 6/2002 | Roe et al. |
| 6,433,244 B1 | 8/2002 | Roe et al. |
| 6,482,491 B1 | 11/2002 | Samuelsen et al. |
| 6,485,476 B1 | 11/2002 | von Dyck et al. |
| 6,524,675 B1 * | 2/2003 | Mikami ................ B32B 37/1284 428/40.1 |
| 6,659,989 B1 | 12/2003 | Otto |
| 6,764,474 B2 | 7/2004 | Nielsen et al. |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,326,190 B2 | 2/2008 | Botten |
| 7,341,578 B2 | 3/2008 | Bulow et al. |
| 7,367,965 B2 | 5/2008 | Poulsen et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 | 3/2010 | McCall |
| 7,943,812 B2 | 5/2011 | Stroebeck et al. |
| 7,981,098 B2 | 7/2011 | Boehringer et al. |
| 3,061,360 A1 | 11/2011 | Locke et al. |
| 8,277,427 B2 | 10/2012 | Edvardsen et al. |
| 8,319,003 B2 | 11/2012 | Olsen et al. |
| 8,398,575 B1 | 3/2013 | McCall |
| 8,398,603 B2 | 3/2013 | Thirstrup et al. |
| 8,399,732 B2 | 3/2013 | Oelund et al. |
| 3,409,158 A1 | 4/2013 | Edvardsen et al. |
| 8,449,471 B2 | 5/2013 | Tran |
| 3,500,718 A1 | 8/2013 | Locke et al. |
| 8,632,492 B2 | 1/2014 | DeLegge |
| 8,680,991 B2 | 3/2014 | Tran |
| 8,684,982 B2 | 4/2014 | Nguyen-Demary et al. |
| 8,740,865 B2 | 6/2014 | Krystek et al. |
| 8,795,257 B2 | 8/2014 | Coulthard et al. |
| 8,821,464 B2 | 9/2014 | Manuka et al. |
| 8,975,465 B2 | 3/2015 | Hong et al. |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,629,964 B2 | 4/2017 | Wuepper |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 | 7/2018 | Thirstrup et al. |
| D826,740 S | 8/2018 | Stevens et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 | 4/2021 | Thirstrup et al. |
| 11,096,818 B2 | 8/2021 | Thirstrup et al. |
| 11,135,084 B2 | 10/2021 | Seres et al. |
| 11,406,525 B2 | 8/2022 | Seres et al. |
| 11,471,318 B2 | 10/2022 | Hansen et al. |
| 2002/0019615 A1 | 2/2002 | Roe et al. |
| 2003/0132763 A1 | 7/2003 | Ellenz |
| 2003/0169032 A1 | 9/2003 | Minchole et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0078219 A1 | 4/2004 | Kaylor et al. |
| 2004/0100376 A1 | 5/2004 | Lye et al. |
| 2004/0111072 A1 | 6/2004 | McKissick |
| 2004/0133175 A1 | 7/2004 | Hagedorn-Olsen |
| 2004/0171999 A1 | 9/2004 | Andersen et al. |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0194324 A1 | 8/2006 | Faries, Jr. et al. |
| 2006/0271002 A1 | 11/2006 | Botten |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2008/0071214 A1 | 3/2008 | Locke et al. |
| 2008/0075934 A1 | 3/2008 | Barlow, Jr. et al. |
| 2008/0091154 A1 | 4/2008 | Botten |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |

(56) References Cited

U.S. PATENT DOCUMENTS

| | | |
|---|---|---|
| 2008/0300559 A1 | 12/2008 | Gustafson et al. |
| 2008/0306459 A1 | 12/2008 | Albrectsen |
| 2009/0012501 A1 | 1/2009 | Boehringer et al. |
| 2009/0118600 A1 | 5/2009 | Ortiz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1* | 2/2010 | Thirstrup ......... A61F 13/00051 604/318 |
| 2010/0036206 A1 | 2/2010 | Lorio |
| 2010/0072271 A1 | 3/2010 | Thorstensson |
| 2011/0034890 A1* | 2/2011 | Stroebech ............... A61F 5/445 604/336 |
| 2011/0077497 A1 | 3/2011 | Oster et al. |
| 2011/0130642 A1 | 6/2011 | Jaeb et al. |
| 2012/0013130 A1 | 1/2012 | Jung |
| 2012/0143154 A1 | 6/2012 | Edvardsen et al. |
| 2012/0143155 A1 | 6/2012 | Edvardsen et al. |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1 | 11/2012 | Nguyen-Demary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0102979 A1 | 4/2013 | Coulthard et al. |
| 2013/0138065 A1* | 5/2013 | Buus ....................... A61F 5/443 604/344 |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0231620 A1 | 9/2013 | Thirstrup et al. |
| 2013/0261575 A1 | 10/2013 | Kiyoshi |
| 2013/0303867 A1 | 11/2013 | Elfstrom et al. |
| 2013/0324952 A1 | 12/2013 | Krystek et al. |
| 2014/0051946 A1 | 2/2014 | Arne et al. |
| 2014/0200538 A1 | 7/2014 | Euliano et al. |
| 2014/0236111 A1 | 8/2014 | Casado et al. |
| 2014/0236335 A1 | 8/2014 | Lewis et al. |
| 2014/0276501 A1 | 9/2014 | Cisko |
| 2014/0288381 A1 | 9/2014 | Faarbaek et al. |
| 2014/0323909 A1 | 10/2014 | Kim |
| 2014/0327433 A1 | 11/2014 | Anway et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0342777 A1 | 12/2015 | Seres et al. |
| 2015/0374896 A1 | 12/2015 | Du et al. |
| 2016/0084869 A1 | 3/2016 | Yuen et al. |
| 2016/0158056 A1 | 6/2016 | Davis et al. |
| 2016/0158969 A1 | 6/2016 | McLane et al. |
| 2016/0166438 A1 | 6/2016 | Rovaniemi |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0284084 A1 | 9/2016 | Gurcan et al. |
| 2016/0305776 A1 | 10/2016 | Martensson et al. |
| 2016/0310140 A1 | 10/2016 | Belson et al. |
| 2016/0310329 A1 | 10/2016 | Patel et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079576 A1 | 3/2017 | Stroebech et al. |
| 2017/0140103 A1 | 5/2017 | Angelides |
| 2017/0156920 A1 | 6/2017 | Hunt et al. |
| 2017/0262986 A1 | 9/2017 | Xiong et al. |
| 2017/0340474 A1 | 11/2017 | Thirstrup et al. |
| 2017/0348137 A1 | 12/2017 | Hvid et al. |
| 2017/0360592 A1 | 12/2017 | Carrubba |
| 2018/0049667 A1 | 2/2018 | Heppe |
| 2018/0055359 A1 | 3/2018 | Shamim et al. |
| 2018/0171183 A1* | 6/2018 | Sakurai ..................... B32B 3/30 |
| 2019/0133810 A1* | 5/2019 | Seres ........................ A61B 5/01 |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0374163 A1 | 12/2019 | Faarbaek et al. |
| 2019/0374372 A1 | 12/2019 | Seres et al. |
| 2020/0100931 A1 | 4/2020 | Schoess et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Munoz Herencia |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0177642 A1 | 6/2021 | Andersen et al. |
| 2021/0212855 A1 | 7/2021 | Hansen et al. |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2022/0000652 A1 | 1/2022 | Thirstrup et al. |
| 2022/0031495 A1 | 2/2022 | Seres et al. |
| 2022/0079802 A1 | 3/2022 | Hansen |
| 2022/0079803 A1 | 3/2022 | Windeballe et al. |

(56) References Cited

U.S. PATENT DOCUMENTS

| | | |
|---|---|---|
| 2022/0087851 A1 | 3/2022 | Stroebech |
| 2022/0117771 A1 | 4/2022 | Feam et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |

FOREIGN PATENT DOCUMENTS

| | | |
|---|---|---|
| CN | 104980878 A | 10/2015 |
| CN | 105588856 A | 5/2016 |
| CN | 206271160 U | 6/2017 |
| CN | 206450708 U | 8/2017 |
| DE | 3437950 A1 | 4/1985 |
| DE | 3836590 A1 | 5/1990 |
| DE | 19953062 A1 | 5/2000 |
| DE | 19900611 C1 | 7/2000 |
| DE | 102011014321 A1 | 9/2012 |
| DE | 102011076219 A1 | 11/2012 |
| EP | 0168967 A1 | 1/1986 |
| EP | 0373782 B1 | 10/1994 |
| EP | 0416397 B1 | 5/1995 |
| EP | 0896211 A2 | 2/1999 |
| EP | 0800804 B1 | 6/2003 |
| EP | 1188157 B1 | 12/2005 |
| EP | 2108345 A1 | 10/2009 |
| EP | 1275357 B1 | 3/2011 |
| EP | 2601915 A1 | 6/2013 |
| EP | 2489561 B1 | 8/2014 |
| EP | 2654646 B1 | 7/2016 |
| EP | 3213727 B1 | 12/2019 |
| GB | 2219679 A | 12/1989 |
| GB | 2343628 A1 | 5/2000 |
| GB | 2465742 B | 7/2012 |
| GB | 2542093 A | 3/2017 |
| JP | H11128352 A | 5/1999 |
| JP | 2001087299 A | 4/2001 |
| JP | 2002055074 A | 2/2002 |
| JP | 2002224093 A | 8/2002 |
| JP | 2005323981 A | 11/2005 |
| JP | 2014033745 A | 2/2014 |
| KR | 20120003987 A | 1/2012 |
| TW | 201201783 A | 1/2012 |
| WO | 1994015562 A1 | 7/1994 |
| WO | 1997010012 A1 | 3/1997 |
| WO | 9933037 A1 | 7/1999 |
| WO | 1999036017 A1 | 7/1999 |
| WO | 0079497 A1 | 12/2000 |
| WO | 2001013830 A1 | 3/2001 |
| WO | 2001050996 A1 | 7/2001 |
| WO | 2002052302 A2 | 7/2002 |
| WO | 2002099765 A1 | 12/2002 |
| WO | 2005082271 A2 | 9/2005 |
| WO | 2006008866 A1 | 1/2006 |
| WO | 2006094513 A2 | 9/2006 |
| WO | 2007000168 A1 | 1/2007 |
| WO | 2007059774 A2 | 5/2007 |
| WO | 2007098762 A1 | 9/2007 |
| WO | 2007133555 A2 | 11/2007 |
| WO | 2008057884 A2 | 5/2008 |
| WO | 2009006900 A1 | 1/2009 |
| WO | 2009052496 A1 | 4/2009 |
| WO | 2009112912 A2 | 9/2009 |
| WO | 2011003421 A1 | 1/2011 |
| WO | 2011004165 A1 | 1/2011 |
| WO | 2011061540 A1 | 5/2011 |
| WO | 2011105701 A2 | 9/2011 |
| WO | 2011123018 A1 | 10/2011 |
| WO | 2011139499 A1 | 11/2011 |
| WO | 2011161254 A2 | 12/2011 |
| WO | 2012068386 A1 | 5/2012 |
| WO | 2012076022 A2 | 6/2012 |
| WO | 2014004207 A1 | 1/2014 |
| WO | 2014086369 A1 | 6/2014 |
| WO | 2015007284 A1 | 1/2015 |
| WO | 2015014774 A1 | 2/2015 |
| WO | 2015084462 A1 | 6/2015 |
| WO | 2016166731 A1 | 10/2016 |
| WO | 2017023794 A1 | 2/2017 |
| WO | 2017062042 A1 | 4/2017 |
| WO | 2017067558 A1 | 4/2017 |
| WO | 2017067560 A1 | 4/2017 |
| WO | 2017088153 A1 | 6/2017 |
| WO | 2017136696 A1 | 8/2017 |
| WO | 2017190752 A1 | 11/2017 |
| WO | 2018028756 A1 | 2/2018 |
| WO | 2019094635 A1 | 5/2019 |
| WO | 2019161863 A1 | 8/2019 |

* cited by examiner

BASE PLATE AND SENSOR ASSEMBLY OF A MEDICAL SYSTEM HAVING A LEAKAGE SENSOR

The present disclosure relates to an ostomy system, devices thereof and method for monitoring an ostomy appliance. The ostomy appliance system comprises an ostomy appliance and an ostomy monitor device. In particular, the present disclosure relates to leakage classification and/or detection and monitoring of the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
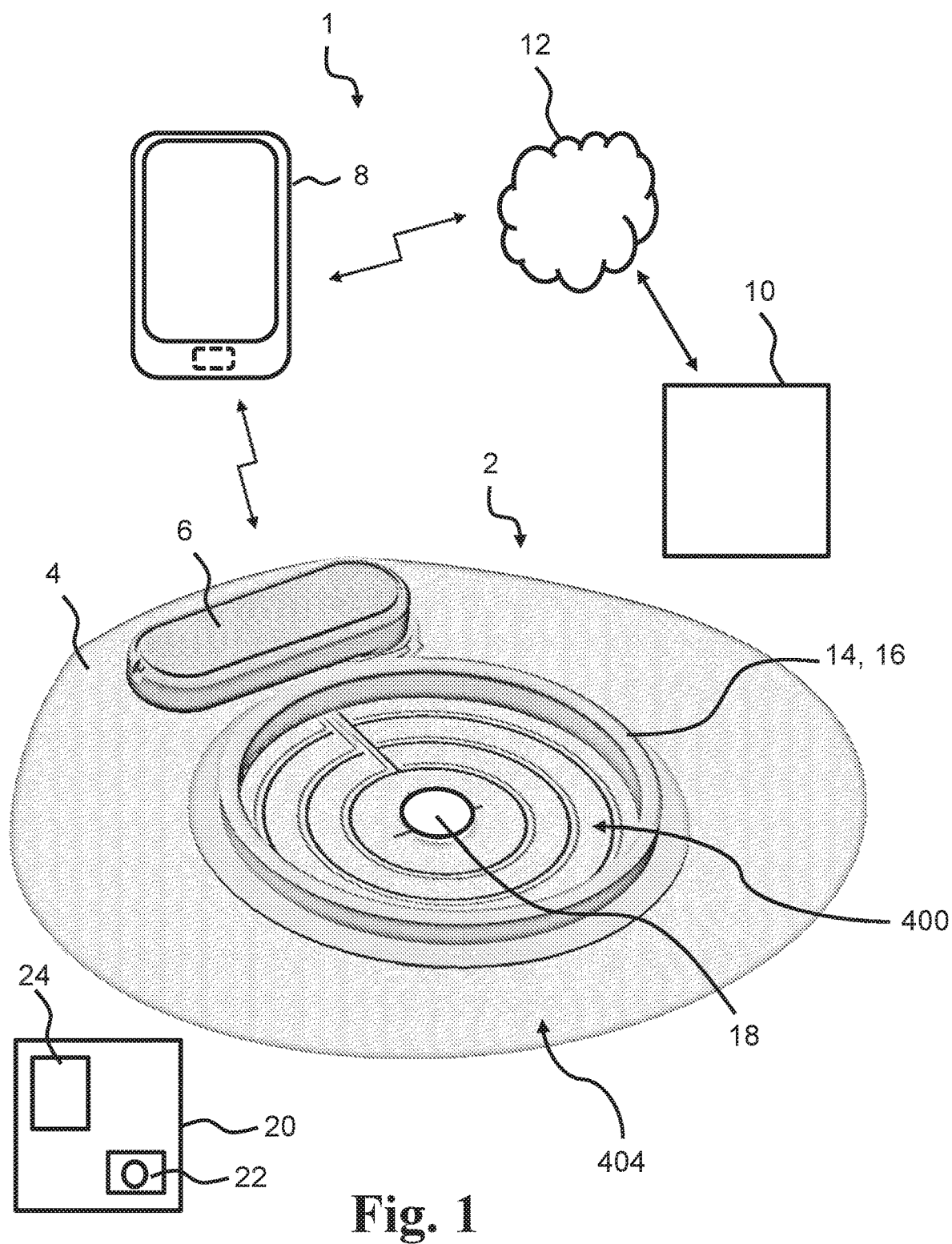
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user.

Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

The base plate and/or the sensor assembly part may comprise a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer may have a stomal opening, such as a first adhesive stomal opening, with a center point.

The first adhesive layer may be made of a first composition. The first composition may comprise one or more polyisobutenes and/or styrene-isoprene-styrene. The first composition may comprise one or more hydrocoloids. The first composition may comprise one or more water soluble or water swellable hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings which may be denoted as a first plurality of openings. A sensor point opening of the first adhesive layer is optionally configured to overlap a part of an electrode, such as a leakage electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode, such as a first leakage electrode, and the primary second sensor point openings configured to overlap parts of another electrode, such as a second leakage electrode, different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode, such as a third leakage electrode, and the secondary second sensor point openings configured to overlap parts of another electrode, such as the second leakage electrode, different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode, such as the third leakage electrode, and the tertiary second sensor point openings configured to overlap parts of another electrode, such as the first leakage electrode, different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be an adhesive layer, also denoted rim adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a center point.

The second adhesive layer may be made of a second composition. The second composition may comprise one or more polyisobutenes and/or styrene-isoprene-styrene. The second composition may comprise one or more hydrocoloids. The second composition may comprise one or more water soluble or water swellable hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIS). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocoloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals/terminal elements. An electrode may comprise one or more conductor parts and/or one or more sensing parts. A conductor part may be considered part of an electrode connecting two or more sensing parts, and/or connecting a sensing part with a connection part of the respective electrode. A sensing part may be considered a part of the electrode being suitable for sensing, e.g. liquid, such as liquid content, and/or output, such as output resulting from a leakage, or an imminent leakage. The sensing part may be suitable for sensing e.g. by its shape, said shape potentially being circular, oval, or rectangular. Thus, the conductor part may conduct a signal arising from the sensing part. An electrode may comprise alternating conductor parts and sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. One of the plurality of electrodes, such as the ground electrode, may form a first leakage electrode. One of the plurality of electrodes, such as the fourth electrode, may form a second leakage electrode. One of the plurality of electrodes, such as the fifth electrode, may form a third leakage electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The fourth electrode and the fifth electrode may form a sixth sensor or sixth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrodes may be prepared by screen-printing, ink-jet-printing, direct-ink-writing, pen-plotting, 3D-printing, fused-deposition-modelling, contact-transfer printing, spray painting, chemical vapour depositing, physical vapour depositing, atomic-layer-depositing, wire-bending, and/or any other methods known to a person skilled in the art. The plurality of electrodes may further require heat-curing, UV-curing, and/or oxygen-activating.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly, such as the support layer of the electrode assembly, may have a stomal opening, such as an electrode assembly stomal opening and/or a support layer stomal opening, with a center point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyimide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate, and/or the sensor assembly part, such as the electrode assembly may comprise a masking element configured to insulate at least parts of the electrodes from the first adhesive layer of the base plate and/or the sensor assembly part. The masking element may comprise one or more, such as a plurality of, sensor point openings which may be denoted as a second plurality of openings. The sensor point openings may comprise primary sensor point openings and/or secondary sensor point openings. The sensor point openings may comprise tertiary sensor point opening(s). The sensor point openings may comprise quaternary sensor point opening(s). A sensor point opening of the masking element overlaps at least one electrode of the electrode assembly when seen in the axial direction, e.g. to form a sensor point. For example, a primary sensor point opening may overlap a part of the ground electrode (e.g. the first leakage electrode) and/or a part of the fourth electrode (e.g. the second leakage electrode). A secondary sensor point opening may overlap a part of the fourth electrode (e.g. the second leakage electrode) and/or a part of the fifth electrode (e.g. the third leakage electrode). A tertiary sensor point opening may overlap a part of the fifth electrode (e.g. the third leakage electrode) and/or a part of the ground electrode (e.g. the first leakage electrode).

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate on the skin. The release liner may have a stomal opening, such as a release liner stomal opening, with a center point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening, such as a top layer stomal opening, with a center point. The top layer may have a thickness in the range from 0.01 mm to 1.0 mm, e.g. in the range from 0.02 mm to 0.2 mm, such as 0.04 mm.

The base plate and/or the sensor assembly part may comprise a monitor interface. The monitor interface may be configured for electrically and/or mechanically connecting the ostomy appliance (base plate and/or sensor assembly part) to the monitor device. The monitor interface may be configured for wirelessly connecting the ostomy appliance (base plate and/or sensor assembly part) to the monitor device. Thus, the monitor interface of the base plate and/or the sensor assembly part may be configured to electrically and/or mechanically couple the ostomy appliance and the monitor device.

The monitor interface of the base plate and/or of the sensor assembly part may comprise, e.g. as part of a first connector of the monitor interface, a coupling part for forming a mechanical connection, such as a releasable coupling between the monitor device and the base plate and/or the sensor assembly part. The coupling part may be configured to engage with a coupling part of the monitor device for releasably coupling the monitor device to the base plate and/or the sensor assembly part.

The monitor interface of the base plate and/or the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or the sensor assembly part, such as the electrode assembly. The first intermediate element may be arranged between the terminal elements and the first adhesive layer. The first intermediate element may cover or overlap terminal element(s) of the base plate and/or the sensor assembly part when seen in the axial direction. Thus, the first adhesive layer may be protected or experience more evenly distributed mechanical stress from the terminal elements of the base plate and/or of the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or the sensor assembly part.

The base plate may comprise a coupling ring or other coupling member for coupling an ostomy pouch to the base plate (two-part ostomy appliance). The center point may be defined as a center of the coupling ring.

The base plate and/or the sensor assembly part may have a stoma-receiving opening with a stoma center point, such as a stomal opening with a center point, alternatively such opening may be denoted a central opening. The stomal opening of the base plate and/or the sensor assembly part may be formed collectively of stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part. The stomal opening may be a through-going passage of the base plate and/or the sensor assembly part. The stomal opening may be arranged substantially in the center of the base plate and/or the sensor assembly part. The stomal opening(s) of the layers of the base plate and/or the sensor assembly part may be arranged substantially in the center of the respective layer. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from a proximal side of the base plate and/or sensor assembly part to a distal side of the base plate and/or sensor assembly part. The size and/or shape of the stomal opening may typically be adjusted by the user or nurse before application of the ostomy appliance to accommodate the user's stoma. In one or more exemplary base plates, the user forms the stomal opening during preparation of the base plate for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate and/or the sensor assembly part of the ostomy appliance based on one or more, such as all, of the first parameter data, the second parameter data and the third parameter data. The operating state may be indicative of a degree of radial erosion of the base plate and/or the sensor assembly part, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate and/or the sensor assembly part via the second interface; and/or in accordance with a determination that the operating state is a second operating state, transmit a second monitor signal comprising monitor data indicative of the second operating state of the base plate and/or the sensor assembly part via the second interface.

In one or more exemplary monitor devices, the first operating state of the base plate and/or the sensor assembly part corresponds to a situation wherein the first adhesive layer of the base plate and/or the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate and/or the sensor assembly part corresponds to a situation wherein the first adhesive layer of the base plate and/or the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate and/or the sensor assembly part is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate and/or the sensor assembly part may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by $$(P\_1\_1 < TH\_1\_1),$$

$$(P\_2\_1 > TH\_1\_2), \text{ and}$$

$$(P\_3\_1 > TH\_1\_3),$$

wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion on the base plate and/or the sensor assembly part. The first threshold values ($TH\_1\_1$, $TH\_1\_2$ and $TH\_1\_3$) may be the same or different, e.g. depending on the electrode configuration of the base plate and/or the sensor assembly part. The first tertiary criterion ($P\_3\_1 < TH\_1\_3$) may be omitted in the first criteria set.

The first primary parameter $P\_1\_1$ may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate and/or the sensor assembly part is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate and/or the sensor assembly part is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by $$(P\_1\_1 < TH\_2\_1),$$

$$(P\_2\_1 < TH\_2\_2), \text{ and}$$

$$(P\_3\_1 > TH\_2\_3)$$

wherein P_1_1 is a first primary parameter based on the first parameter data and indicative of the resistance between the first electrode pair, TH_2_1 is a second primary threshold value, P_2_1 is a second primary parameter based on the second parameter data and indicative of the resistance between the second electrode pair, TH_2_2 is a second secondary threshold value, P_3_1 is a third primary parameter based on the third parameter data and indicative of the resistance between the third electrode pair, TH_2_3 is a second tertiary threshold value, and wherein the second operating state is indicative of medium degree of radial erosion on the base plate and/or the sensor assembly part. The second threshold values (TH_2_1, TH_2_2 and TH_2_3) may be the same or different, e.g. depending on the electrode configuration of the base plate and/or the sensor assembly part. The second primary criterion (P_1_1<TH_2_1) and/or the second tertiary criterion (P_3_1>TH_2_3) may be omitted in the second criteria set.

In one or more exemplary monitor devices, to determine an operating state of the base plate and/or the sensor assembly part is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by $$(P\_1\_1 > TH\_D\_1),$$

$$(P\_2\_1 > TH\_D\_2), \text{ and}$$

$$(P\_3\_1 > TH\_D\_3)$$

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate and/or the sensor assembly part. The default threshold values (TH_D_1, TH_D_2 and TH_D_3) may be the same or different, e.g. depending on the electrode configuration of the base plate and/or the sensor assembly part.

In one or more exemplary monitor devices, to determine an operating state of the base plate and/or the sensor assembly part is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate and/or the sensor assembly part corresponds to a situation wherein the first adhesive layer of the base plate and/or the sensor assembly part has experienced a third degree of radial erosion, e.g. the first adhesive layer is eroded to the third radial distance of the third electrode pair.

The third criteria set may be given by $$(P\_1\_1 < TH\_3\_1),$$

$$(P\_2\_1 < TH\_3\_2), \text{ and}$$

$$(P\_3\_1 < TH\_3\_3)$$

wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate and/or the sensor assembly part. The third threshold values (TH_3_1, TH_3_2 and TH_3_3) may be the same or different, e.g. depending on the electrode configuration of the base plate and/or the sensor assembly part. The third primary criterion (P_1_1<TH_3_1) and/or the third secondary criterion (P_2_1<TH_3_2) may be omitted in the third criteria set.

In one or more exemplary monitor devices, the ostomy data comprises fourth ostomy data from a fourth electrode pair (e.g. first leakage electrode and second leakage electrode) of the base plate and/or the sensor assembly part. To apply a processing scheme may comprise to obtain fourth parameter data based on the fourth ostomy data, and determine an operating state of the base plate and/or the sensor assembly part of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate and/or the sensor assembly part corresponds to a situation, wherein the fourth electrode pair detects fluid, such as output, between the distal surface of first adhesive layer and the skin of the user at a fourth radial distance and/or within a fourth angle space, and thus there is a high risk of leakage from the ostomy appliance in the fourth operating state.

The fourth criteria set may be given by $$(P\_4\_1 < TH\_4\_4)$$

wherein P_4_1 is a fourth primary parameter based on the fourth parameter data and indicative of the resistance between the fourth electrode pair and TH_4_4 is a fourth quaternary threshold value, and wherein the fourth operating state is indicative of high risk of leakage from the ostomy appliance.

In one or more exemplary monitor devices, the ostomy data comprises fifth ostomy data from a fifth electrode pair (e.g. third leakage electrode and second leakage electrode)

of the base plate and/or the sensor assembly part. To apply a processing scheme may comprise to obtain fifth parameter data based on the fifth ostomy data, and determine an operating state of the base plate and/or the sensor assembly part of the ostomy appliance based on the fifth parameter data. The monitor device may be configured to, in accordance with a determination that the operating state is a fifth operating state, transmit a fifth monitor signal comprising monitor data indicative of the fifth operating state of the ostomy appliance.

In one or more exemplary monitor devices, the fifth operating state of the base plate and/or the sensor assembly part corresponds to a situation, wherein the fifth electrode pair detects fluid, such as output, between the distal surface of first adhesive layer and the skin of the user at a fifth radial distance and/or within a fifth angle space, and thus there is a high risk of leakage from the ostomy appliance in the fifth operating state.

The fifth criteria set may be given by $$(P\_5\_1 < TH\_5\_5)$$

wherein P_5_1 is a fifth primary parameter based on the fifth parameter data and indicative of the resistance between the fifth electrode pair and TH_5_5 is a fifth quinary threshold value, and wherein the fifth operating state is indicative of high risk of leakage from the ostomy appliance.

In one or more exemplary monitor devices, the ostomy data comprises sixth ostomy data from a sixth electrode pair (e.g. third leakage electrode and first leakage electrode) of the base plate and/or the sensor assembly part. To apply a processing scheme may comprise to obtain sixth parameter data based on the sixth ostomy data, and determine an operating state of the base plate and/or the sensor assembly part of the ostomy appliance based on the sixth parameter data. The monitor device may be configured to, in accordance with a determination that the operating state is a sixth operating state, transmit a sixth monitor signal comprising monitor data indicative of the sixth operating state of the ostomy appliance.

In one or more exemplary monitor devices, the sixth operating state of the base plate and/or the sensor assembly part corresponds to a situation, wherein the sixth electrode pair detects fluid, such as output, between the distal surface of first adhesive layer and the skin of the user at a sixth radial distance and/or within a sixth angle space, and thus there is a high risk of leakage from the ostomy appliance in the sixth operating state.

The sixth criteria set may be given by $$(P\_6\_1 < TH\_6\_6)$$

wherein P_6_1 is a sixth primary parameter based on the sixth parameter data and indicative of the resistance between the sixth electrode pair and TH_6_6 is a sixth senary threshold value, and wherein the sixth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped. Additionally or alternatively, the monitor device may be rigid or flexible.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and//or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery. Additionally, or alternatively, the sensor terminal may change its function if the charging voltage is sensed at relevant terminals.

The monitor device may comprise a sensor unit with one or more sensors. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, and Bluetooth 5. The second interface optionally comprises a loudspeaker and/or a haptic feedback element for provision of an audio signal and/or haptic feedback to the user, respectively.

The monitor device may be electrically coupled to the plurality of electrodes of the base plate and/or the sensor assembly part. For example, the monitor device may be couplable, such as releasably couplable, to the plurality of electrodes of the base plate and/or the sensor assembly part. The monitor device may be configured to measure one or more resistances between the plurality of electrodes, and detect the leakage of output, such as one or more indications of the leakage of output, based on the measured one or more resistances.

In one or more exemplary ostomy systems, the monitor device forms an integrated part of the ostomy appliance, e.g. the monitor device may form an integrated part of a base plate and/or the sensor assembly part of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

Disclosed is an ostomy system, such as an ostomy system as disclosed above, e.g. configured to detect a leakage of output, such as one or more indications of leakage of output between a base plate and/or a sensor assembly part of the ostomy system and a surface of a subject, such as a subject wearing the base plate.

Also disclosed is a base plate a sensor assembly part and a monitor device, as also described above. The ostomy system may comprise the base plate, and/or the sensor assembly part, and/or a monitor device. The base plate and/or the sensor assembly part may be at least one of bendable, flexible, twistable, and stretchable.

The base plate and/or the sensor assembly part includes a first adhesive layer, such as the first adhesive layer as also described above, having a distal surface, a proximal surface, and a first plurality of openings. The proximal surface may be configured for attachment of the base plate and/or sensor assembly part to the skin surface of a user, such as a peristomal skin surface of the user. The first adhesive layer may have a stomal opening with a center point.

The base plate and/or the sensor assembly part includes an electrode assembly, such as the electrode assembly as described above, disposed on the distal surface of the first adhesive layer.

The electrode assembly includes a plurality of electrodes. The electrode assembly includes a masking element between the plurality of electrodes and the first adhesive layer. The masking element has a second plurality of openings aligned with the first plurality of openings of the first adhesive layer to form a plurality of sensor point openings. Each of the aligned first and second plurality of openings, such as the sensor point openings, exposes a portion of one of the plurality of electrodes to define one of a plurality of sensor points. The aligned first and second plurality of openings, such as the sensor point openings, may provide a plurality of conduits at the plurality of sensor points, e.g. exposing the portions of the plurality of electrodes.

The plurality of sensor points may comprise a plurality of sensor point groups, e.g. including primary sensor points, secondary sensor points, and tertiary sensor points. Each of the sensor point groups may expose sensor parts of an electrode of the plurality of electrodes. For example, each of the primary sensor points may include an exposed portion of a first leakage electrode, such as the ground electrode, of the plurality of electrodes. Each of the secondary sensor points may include an exposed portion of a second leakage electrode, such as the fourth electrode, of the plurality of electrodes. Each of the tertiary sensor points may include an exposed portion of a third leakage electrode, such as the fifth electrode, of the plurality of electrodes. The plurality of sensor points may be distributed alternatingly. For example, such that the nearest sensor point from a primary sensor point, such as any of the primary sensor points, is a secondary sensor point and/or a tertiary sensor points. The nearest sensor point from a primary sensor point may not be another of the primary sensor points. In such arrangement, two different electrodes may be exposed within the same vicinity, which facilitates the detection of the leakage of output, such as the one or more indications of leakage of output.

The monitor device may be electrically coupled to the plurality of electrodes of the base plate and/or the sensor assembly part. For example, the monitor device may be couplable, such as releasably couplable, to the plurality of electrodes of the base plate and/or the sensor assembly part. The monitor device may be configured to measure one or more resistances between the plurality of electrodes, and detect the leakage of output, such as the one or more indications of leakage of output based on the measured one or more resistances.

The base plate and/or the sensor assembly part may be configured to detect the leakage of output, such as the one or more indications of leakage of output, by way of detecting short-circuit events via the plurality of electrodes. For example, a first leakage electrode and a second leakage electrode of the plurality of electrodes can be configured to short-circuit through the leakage of output, e.g. when the leakage of output connects the first leakage electrode and the second leakage electrode at a first sensor point and a second sensor point of the plurality of sensor points.

One of a plurality of sensor point openings, such as a first sensor point opening, may expose a portion of the first leakage electrode at the first sensor point. Another of the plurality of sensor point openings, such as a second sensor point opening, may expose a portion of the second electrode at the second sensor point. Another of the plurality of sensor point openings, such as a third sensor point opening, may expose a portion of the third electrode at a third sensor point. The sensor point openings provide the leakage of output a way to contact the first, second and/or third electrodes, such as to create a less resistive pathway compared to a pathway through the first adhesive layer. Thereby, the first, second and/or third leakage electrodes may be short-circuited by output connecting the first sensor points and the second sensor point. The resistance measured between the first, second and/or third leakage electrodes may, as a result, decrease. Decrease of resistance between the first, second and/or third leakage electrodes may be indicative of the less resistive pathway created by the leakage of output.

The ostomy system may be configured to detect the leakage of output, such as the one or more indications of leakage of output, propagating from a central region of the base plate and/or the sensor assembly part towards any direction in a base plane, e.g. defined by the proximal surface of the first adhesive layer. For example, the ostomy system may be configured to detect, using the one or more resistances measured by the monitor device via the plurality of electrodes, the leakage of output and/or the one or more indications of leakage of output propagating from the central region of the base plate and/or the sensor assembly part towards any direction in the base plane.

The base plate and/or the sensor assembly part may comprise one or more sensing zones. The one or more sensing zones may include a first sensing zone and a second sensing zone and/or a third sensing zone. Each of the one or more sensing zones may include at least parts, such as sensing parts, of two of the plurality of electrodes.

The plurality of sensor point openings may comprise a plurality of primary sensor point openings in the first sensing zone. The plurality of sensor point openings may comprise a plurality of secondary sensor point openings in the second sensing zone. The plurality of sensor point openings may comprise a plurality of tertiary sensor point openings in the third sensing zone. The plurality of primary sensor point openings may comprise one or more primary first sensor point openings exposing a portion of a first leakage electrode, such as the ground electrode, of the plurality of electrodes. The plurality of primary sensor point openings may comprise one or more primary second sensor point openings exposing a portion of a second leakage electrode, such as the fourth electrode, of the plurality of electrodes. The plurality of secondary sensor point openings may comprise one or more secondary first sensor point openings exposing a portion of a third leakage electrode, such as the fifth electrode, of the plurality of electrodes. The plurality of secondary sensor point openings may comprise one or more secondary second sensor point opening exposing a portion of the second leakage electrode, such as the fourth electrode, of the plurality of electrodes. The plurality of tertiary sensor point openings may comprise one or more tertiary first sensor point openings exposing a portion of the third leakage electrode, such as the fifth electrode, of the plurality of electrodes. The plurality of tertiary sensor point openings may comprise one or more tertiary second sensor point opening exposing a portion of the first leakage electrode, such as the ground electrode, of the plurality of electrodes.

The one or more sensing zones may be distributed at least one of circularly, such as angularly, about, radially from, and concentrically about a central opening, such as a stomal opening, of the base plate and/or the sensor assembly part. For example, the one or more sensing zones may be distributed angularly about the central opening of the base plate and/or the sensor assembly part. Alternatively or additionally, the one or more sensing zones may be distributed radially about the central opening of the base plate and/or the sensor assembly part. Alternatively or additionally, the one or more sensing zones may be distributed concentrically about the central opening of the base plate and/or the sensor assembly part. Such distribution of sensing zones may help detect the leakage of output and/or one or more indications of leakage of output, such as leakage of output propagating from the central region of the base plate and/or the sensor assembly part outwards to an outer region of the base plate and/or the sensor assembly part, e.g. in any direction within the base plane. Sweat will normally be evenly distributed underneath the base plate and/or the sensor assembly part, while output will normally be localized to a specific region (or perhaps two neighboring regions). Thus, difference between measured values of different sensing zones may be used to differentiate between sweat and output.

The one or more sensing zones, such as a plurality of the one or more sensing zones, may be spaced radially and/or angularly with respect to a center point of the stomal opening.

For example, the first sensing zone may be arranged in a first angle space from the center point, the second sensing zone may be arranged in a second angle space from the center point, and/or the third sensing zone may be arranged in a third angle space from the center point. The first angle space may span a first angle in the range from 45° to 315°, such as in the range from 45° to 135°. The second angle space may span a second angle in the range from 45° to 315°, such as in the range from 45° to 135°. The third angle space may span a third angle in the range from 45° to 315°, such as in the range from 45° to 135°. The first, second, and/or third angle may depend on the number of angular sensing zones on the base plate and/or the sensor assembly part. For example, the first, second and/or third angle may be about 180°±15°, e.g. for a base plate and/or a sensor assembly part with two or more angular sensing zones. The first, second and/or third angle may be about 120°±15°, e.g. for a base plate and/or a sensor assembly part with two, three or more sensing zones. The first, second and/or third angle may be about 90°±15°, e.g. for a base plate and/or a sensor assembly part with two, three, four or more sensing zones.

Alternatively or additionally, the first sensing zone may be arranged in a first radial space from the center point, the second sensing zone may be arranged in a second radial space from the center point, and/or the third sensing zone may be arranged in a third radial space from the center point. The first radial space may span a primary radius in the range from 5-50 mm, such as in the range from 10-25 mm, such as in the range from 13-14 mm. The second radial space may span a second radius in the range from 10-50 mm, such as in the range from 10-25 mm, such as in the range from 25-26 mm. The third radial space may span a third radius in the range from 15-50 mm, such as in the range from 25-50 mm, such as in the range from 29-30 mm. The first, second and/or third radius may depend on the number of radial sensing zones on the base plate and/or the sensor assembly part. The second radius may be greater than the first radius. The third radius may be greater than the second radius and/or the first radius.

Each of the one or more sensing zones may include at least sensing parts of two of the plurality of electrodes, e.g. such that each of the one or more sensing zones may be generally defined, outlined, designated, and/or specified by two of the plurality of electrodes. For example, the first leakage electrode and the second leakage electrode, such as the ground electrode and the fourth electrode, of the plurality of electrodes may define the first sensing zone. Alternatively or additionally, the second leakage electrode and the third leakage electrode, such as the fourth electrode and the fifth electrode, of the plurality of electrodes may define the second sensing zone. Alternatively or additionally, the first leakage electrode and the third leakage electrode, such as the ground electrode and the fifth electrode, of the plurality of electrodes may define the third sensing zone. One or more of the plurality of electrodes may be in a plurality of the one or more sensing zones.

The one or more sensing zones may include a fourth sensing zone and/or a fifth sensing zone and/or a sixth sensing zone. For example, the first leakage electrode and a fourth leakage electrode, such as the ground electrode and a sixth electrode, of the plurality of electrodes may define the fourth sensing zone. Alternatively or additionally, the second leakage electrode and the fourth leakage electrode, such as the fourth electrode and the sixth electrode, of the plurality of electrodes may define the fifth sensing zone. Alternatively or additionally, the fourth leakage electrode and the third leakage electrode, such as the sixth electrode and the fifth electrode, of the plurality of electrodes may define the sixth sensing zone.

Each of the one or more sensing zones may include at least sensing parts of two of the plurality of sensor point groups, wherein each of the two of the plurality of sensor point groups exposes portions of one of the plurality of electrodes. For example, the first sensing zone may comprise some of the primary sensor points and some of the secondary sensor points. The second sensing zone may comprise some of the secondary sensor points and some of the tertiary sensor points. The third sensing zone may comprise some of the primary sensor points and some of the tertiary sensor points.

The first adhesive layer may have a first electrical conductivity. The masking element may have a second electrical conductivity. Output may have a third electrical conductivity. The second electrical conductivity may be lower than the first electrical conductivity. Alternatively or additionally, the third electrical conductivity may be higher than the first electrical conductivity.

The first adhesive layer may be air permeable, such as at least slightly air permeable, e.g. to help the leakage of output enter the plurality of conduits at the plurality of sensor points with minimal resistive pressures created by the leakage of output compressing the air in the plurality of conduits. The plurality of conduits may be configured for the leakage of output to easily enter such that the ostomy system may register the leakage signal, e.g. by detecting the short-circuit event, less than 1 second from the leakage of output entering the corresponding sensing zone.

The masking element may comprise at least one of polymeric and ceramic materials. For example, the masking element may comprise polymeric materials. Alternatively or additionally, the masking element may comprise ceramic materials.

The plurality of electrodes may comprise at least one of metallic, ceramic, polymeric, and carbonaceous materials. For example, the plurality of electrodes may comprise metallic materials. Alternatively or additionally, the plurality of electrodes may comprise ceramic materials. Alternatively or additionally, the plurality of electrodes may comprise polymeric materials. Alternatively or additionally, the plurality of electrodes may comprise carbonaceous materials. The plurality of electrodes may comprise one of silver and carbon. For example, the plurality of electrodes may comprise silver. Alternatively or additionally, the plurality of electrode may comprise carbon.

The base plate and/or the sensor assembly part may comprise, such as further comprise, a second adhesive layer. The second adhesive layer may be coupled distally to the first adhesive layer and the electrode assembly. For example, the second adhesive layer may be attached to the distal side of the electrode assembly and/or first adhesive layer. The second adhesive layer may be at least one of more adhesive to the surface of the subject, more moisture permeable, less moisture-absorbent, and lower in moisture capacity than the first adhesive layer. For example, the second adhesive layer may be more adhesive to the surface of the subject than the first adhesive layer. Alternatively or additionally, the second adhesive layer may be more moisture permeable than the first adhesive layer. Alternatively or additionally, the second adhesive layer may be less moisture-absorbent than the first adhesive layer. Alternatively or additionally, the second adhesive layer may have a lower moisture capacity than the first adhesive layer. The adhesive properties may be selected to obtain desired sensing range, sensing responsiveness, adhesive security, and/or prolonged usable time of the base plate.

The base plate and/or the sensor assembly part may comprise, such as further comprise, a release liner. The release liner may be releasably attached to a proximal surface of the first adhesive layer. The release liner may have a plurality of protrusions configured to extend into the first plurality of openings of the first adhesive layer. The plurality of protrusions of the release liner may preserve the openings in the first adhesive layer, since the first adhesive layer may exhibit viscous properties. Thereby, shelf life of the base plate and/or the sensor assembly part may be extended.

The base plate and/or the sensor assembly part may comprise, such as further comprise, a first intermediate element, e.g. between the first adhesive layer and a plurality of connection parts of the plurality of electrodes. The first intermediate element may be between the first adhesive layer and the plurality of connection parts to shield the connections parts from the first adhesive layer. For example, the electrical conductivity may change as a function of moisture content in the first adhesive layer. Thus, shielding the connection parts from the first adhesive layer may decrease the change in conductivity between electrodes caused by changing moisture content of the first adhesive layer near the connection parts.

The first intermediate element may be less electrically conductive than the first adhesive layer, e.g. such that the resistance measurement is not influenced by the first intermediate element near the connection parts of the plurality of electrodes.

The electrode assembly may further comprise a support layer coupled to the plurality of electrodes, e.g. to provide additional structural integrity for the electrode assembly that includes the plurality of electrodes. For example, the plurality of electrodes may have been printed onto the support layer. The support layer may have a greater structural integrity than the first adhesive layer. For example, the support layer may be less stretchable than the first adhesive layer.

The first adhesive layer and/or the second adhesive layer may comprise a hydrocolloid and/or a polymer matrix, e.g. such that the first adhesive layer and/or the second adhesive layer is moisture absorbent.

The first adhesive layer may have a smaller surface coverage than the second adhesive layer. The first adhesive layer and/or the second adhesive layer may have bigger surface coverage than the plurality of electrodes and/or the electrode assembly. Thereby, the plurality of electrodes and/or the electrode assembly may be encapsulated by adhesive, e.g. the first adhesive layer and the second adhesive layer, and the first adhesive layer and the second adhesive layer may be attached along a rim portion of the first adhesive layer and/or the second adhesive layer.

The monitor device may be configured to generate a leakage signal, e.g. when the leakage of output is detected and/or when the one or more indications of the leakage of output is detected, such as detected in at least one of the one or more sensing zones.

The monitor device may be configured to determine rate of change of each of the one or more resistances measured in the one or more sensing zones. For example, the monitor device may be configured to determine a first rate of change of the first resistance measured in the first sensing zone, the monitor device may be configured to determine a second rate of change of the second resistance measured in the second sensing zone, and/or the monitor device may be configured to determine a third rate of change of the third resistance measured in the third sensing zone. The rate of change may be different depending on the cause of the change, e.g. whether the change is caused by output or sweat. The monitor device may be configured to generate the leakage signal based on the determined rate of change, such as the first, second and/or third rate of change. The rate of change may be indicative of a presumed cause of the change of resistance in the one or more sensing zone, such as the first, second and/or third sensing zone. The monitor device may be configured to generate the leakage signal if the determined rate of change is above a first rate threshold. The monitor device may be configured to forgo generation of the leakage signal if the determined rate of change is below a second rate threshold. The first rate threshold may be the same as the second rate threshold. Alternatively, the first rate threshold may be greater than the second rate threshold.

It may be useful to introduce an instant relative decay (IRD) in order to differentiate leakage from moisture absorption. The IRD is equal to the difference (typically a fall in resistance, i.e. a decay) between a measured data point (e.g. a numerical value of the resistance across a sensor) and the previously measured data point (e.g. another numerical value of the resistance across a sensor), divided by the maximum possible difference (decay). The maximum decay may be the situation going from a baseline measurement of a healthy base plate and/or sensor assembly part, to a situation where the resistance has fallen to zero, i.e. indicative of a short-circuited sensor. Thus, the instant relative decay (IRD) is given by;

$$IRD = \frac{|A_2 - A_1|}{A_{max}} \times 100\%$$

where $A_2$ and $A_1$ are the previously measured data point (at time $t_2$) and the present data point (at time $t_1$), respectively, and where Amax is the largest possible decay. For resistance measurements, Amax may be the absolute value of the resistance across a sensor in a healthy base plate and/or sensor assembly part. The difference $A_2-A_1$ may be denominated an actual decay, as it relates to the decay in the measured parameter at present relative to the previously measured value of the parameter. Preferably, the modulus (absolute value) of the actual decay is considered.

The monitor device and/or the accessory device may be configured to determine an instant relative decay based on the measured resistance measured across the one or more sensors and/or in the one or more sensing zones. Therefrom, the monitor device and/or the accessory device may be configured to determine the condition of the base plate/and or the sensor assembly part.

It should be noted that other parameters than resistance may be monitored, as described previously. Further, it should be noted that the formula does not require a certain unit (for resistance measurements; ohm), as only a relative change is considered. As such, a signal proportional to the resistance across the sensor is sufficient to calculate the IRD.

The data point sampling rate may be from 1 Hz (every second) to 0.017 Hz (every 60th second), or even higher or lower, depending on the settings of the monitor device and/or the accessory device. A higher sampling rate results in a higher power usage. Thus, the difference $t_2-t_1$ may correspond the interval between consecutively measured data points according to the given data point sampling rate. The data point sampling rate may be adaptive to the condition of the base plate and/or the sensor assembly plate. For example, the sampling rate may be increased if a tendency of increasing IRD is observed. Thereby, power is saved when the base plate and/or the sensor assembly part is considered healthy, and may instead be directed to the situation where the base plate and/or the sensor assembly part is deteriorating.

The monitor device and/or the accessory device may determine/calculate the IRD based on the measured raw data. Alternatively, the monitor device and/or the accessory device may determine/calculate a moving average based on the measured raw data prior to determining/calculating the IRD. Thus, the monitor device/and or the accessory device may determine/calculate the IRD based on the moving average of the raw data. The moving average may be an exponential moving average or a simple moving average. Introducing a moving average serves to reduce the significance of false signals. From the moving average, the monitor device and/or the accessory device may determine/calculate the derivative, which emphasizes changes in the measured data points, i.e. changes in the resistance. The monitor device and/or the accessory device may determine/calculate the IRD from the derivative of the calculated moving average.

The IRD allows for a mathematical treatment and differentiation of leakage and moisture absorption. In particular, the IRD allows for the differentiation of leakage and expel of sweat. A threshold of 60%, of 70%, of 80%, or of 90% may be introduced to specify leakage. The threshold may be adaptive to the individual user, such that a lower or higher percentage may be used as the threshold to define a leakage. As an example, an IRD of 80% indicates an instant drop in resistance of 80%, which may indicate a sudden presence of output, i.e. a leakage. In case the threshold is set at 80%, the calculated IRD of more than, or equal to, 80% is considered leakage of output, whereas an IRD of less than 80% is considered moisture absorption, e.g. resulting from an excessive expel of sweat. Thus, the monitor device and/or the accessory device may determine whether a calculated IRD falls below or above a threshold value. The monitor device and/or the accessory device may be configured to generate a leakage signal if the calculated IRD is above the threshold value.

In the case of an electrode assembly divided into sensing zones, the above discussed mathematical process of differentiating a leakage from moisture absorption or expel of sweat may be applied to each sensing zone. Thus, the monitor device and/or the accessory device may be configured to determine/calculate the IRD for each of the one or more sensing zones of the base plate and/or sensor assembly part. Likewise, the derivative of the moving average may be used to monitor the health of the baser plate and/or the sensor assembly part by analysing the changes of resistance. Thus, the monitor device and/or the accessory device may be configured to apply the derivative to a forecast model for forecasting the health of the base plate and/or the sensor assembly part.

A leakage signal may comprise at least one of leakage location, leakage propagating direction, and leakage propagating velocity. The leakage location may comprise the sensing zones where short-circuit events have been detected. Additionally, the leakage location may comprise a region between the sensing zones where the short-circuit events have been detected.

The leakage propagating direction may comprise a direction from one of the one or more sensing zones that first registered a short-circuit event, to another of the one or more sensing zones that next registered a short-circuit event. The leakage propagating direction may be substantially parallel to the base plate and/or the sensor assembly part and/or the base plane. The leakage propagating velocity may comprise a velocity derived by dividing the distance between the two sensing zones where short-circuit events have sequentially been detected, by a time-delay between the detection of short-circuit events at the two sensing zones.

Leakage of output may be detected, e.g. one or more indications of leakage of output may be detected, e.g. based on the measured one or more resistances. The detection of leakage of output, such as detection of one or more indications of leakage of output, may comprise determining that the leakage of output is present, e.g. when one or more of the one or more resistances measured, e.g. at one or more of the one or more sensing zones, is smaller or equal to one of one or more threshold resistances. Different threshold resistances may be employed for different sensing zones, e.g. to reflect different electrode characteristics such as length or inter-electrode spacing. For example, a first threshold resistance may be employed for the first sensing zone, a second threshold resistance may be employed for the second sensing zone, and/or a third threshold resistance may be employed for the third sensing zone.

The ostomy system may be configured to provide warning to the user based on the detection of leakage of output, such as detection of one or more indications of leakage of output, e.g. such that the base plate may be replaced before the leakage of output exits the containment of the ostomy appliance, such as the base plate.

Also disclosed is a method of detecting a leakage of output, such as detection of one or more indications of leakage of output, between a base plate and/or the sensor assembly part of an ostomy system and a surface of a subject, such as a subject wearing the base plate and/or the sensor assembly part.

The ostomy system may be the ostomy system as disclosed above. For example, the ostomy system includes the base plate and/or the sensor assembly part and a monitor device. The base plate and/or the sensor assembly part comprises (i) a first adhesive layer having a distal surface, a proximal surface, and a first plurality of openings, the proximal surface may be configured for attachment of the base plate to the skin surface of a user, and (ii) an electrode assembly comprising a plurality of electrodes and a masking element between the plurality of electrodes and the first adhesive layer. The masking element has a second plurality of openings aligned with the first plurality of openings of the first adhesive layer, e.g. to form a plurality of sensor point openings. Each of the aligned first and second plurality of openings, such as the plurality of sensor point openings, exposes a portion of one of the plurality of electrodes to define one of a plurality of sensor points. The monitor device is electrically coupled and/or couplable, such as releasably couplable, to the plurality of electrodes of the base plate and/or the sensor assembly part.

The method may comprise measuring, e.g. via the plurality of electrodes, one or more resistances. Each of the one or more resistances measured between two of the plurality of electrodes. The method may comprise detecting the leakage of output, such as detecting one or more indications of leakage of output, based on the measured one or more resistances.

Measuring one or more resistances, e.g. between the plurality of electrodes, may comprise measuring each of the one or more resistances in one of one or more sensing zones. The one or more sensing zones may include a first sensing zone, a second sensing zone and/or a third sensing zone.

Measuring one or more resistances, e.g. between the plurality of electrodes, may comprise measuring each of the one or more resistances between two of the plurality of electrodes, wherein portions of each of the two of the plurality of electrodes are exposed by some of a plurality of conduits, such as the sensor point openings, at some of the plurality of sensor points of the same sensing zone, such as the first sensing zone, the second sensing zone and/or the third sensing zone.

Measuring one or more resistances, e.g. between the plurality of electrodes, may comprise measuring a first resistance in a first sensing zone and measuring a second resistance in a second sensing zone. Measuring one or more resistances, e.g. between the plurality of electrodes, may comprise measuring a third resistance in a third sensing zone. The first resistance may be measured between a first leakage electrode, such as a ground electrode, and a second leakage electrode, such as a fourth electrode, of the plurality of electrodes. The first leakage electrode, such as the ground electrode, may be exposed at a first sensor point in the first sensing zone. The second leakage electrode, such as the fourth electrode may be exposed at a second sensor point in the first sensing zone. The second resistance may be measured between the second leakage electrode, such as the fourth electrode, and a third leakage electrode, such as a fifth electrode of the plurality of electrodes. The second leakage electrode, such as the fourth electrode, may be exposed at a third sensor point in the second sensing zone. The third leakage electrode, such as the fifth electrode may be exposed at a fourth sensor point in the second sensing zone. The first resistance may be measured between the first leakage electrode, such as the ground electrode and the third leakage electrode, such as the fifth electrode, of the plurality of electrodes. The first leakage electrode, such as the ground electrode may be exposed at a fifth sensor point in the third sensing zone. The third leakage electrode, such as the fifth electrode may be exposed at a sixth sensor point in the third sensing zone.

Measuring one or more resistances, e.g. between the plurality of electrodes, may comprise measuring each of the one or more resistances in one of one or more sensing zones between two of the plurality of electrodes, wherein portions of each of the two of the plurality of electrodes are exposed by some of a plurality of conduits, such as of the plurality of sensor point openings, at some of the plurality of sensor points such that the leakage of output may contact both of the two of the plurality of electrodes by entering two or more of the plurality of conduit, such as the plurality of sensor point openings, s to create a less resistive path for measuring resistance between the two of the plurality of electrodes.

The measuring, between the plurality of electrodes, one or more resistances may comprise measuring each of the one or more resistances in one or more sensing zones including a first sensing zone and a second sensing zone. A first resistance of the one or more resistances may be measured for the first sensing zone and a second resistance of the one or more resistances may be measured for the second sensing zone. The first resistance may be measured between two of the plurality of electrodes being exposed by some of a plurality of conduits, such as of the plurality of sensor point openings, at some of the plurality of sensor points in the first sensing zone. The second resistance may be measured between two of the plurality of electrodes being exposed by some of the plurality of conduits, such as of the plurality of sensor point openings, at some of the plurality of sensor points in the second sensing zone.

Detecting the leakage of output, such as detecting one or more indications of leakage of output, e.g. based on the measured one or more resistances, may comprise determining that the leakage of output is present, e.g. when one or more of the one or more resistances measured, e.g. at one or more of one or more sensing zones, is smaller or equal to one of one or more threshold resistances. Different threshold resistances may be employed for different sensing zones, e.g. to reflect different electrode characteristics such as length or inter-electrode spacing. For example, a first threshold resistance may be employed for the first sensing zone, a second threshold resistance may be employed for the second sensing zone, and/or a third threshold resistance may be employed for the third sensing zone.

The method may further comprise generating a leakage signal, e.g. through the monitor device when the leakage of output has been detected, such as when the one or more indications of leakage of output has been detected.

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data. Based on the processed ostomy data, the monitor device 6 may determine what monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma center point. The size and/or shape of the stomal opening 18 are typically adjusted by the user or nurse before application of the ostomy appliance to accommodate the user's stoma. The base plate may have a central region 400 and an outer region 404. The central region 400 is the region near the stomal opening 18 and/or substantially equal to the region within the coupling member 14. The outer region 404 is the region farther from the stomal opening 18 and/or substantially equal to the region outside of the coupling member 14.

The ostomy system 1 optionally comprises a docking station 20 forming an alternative/additional accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
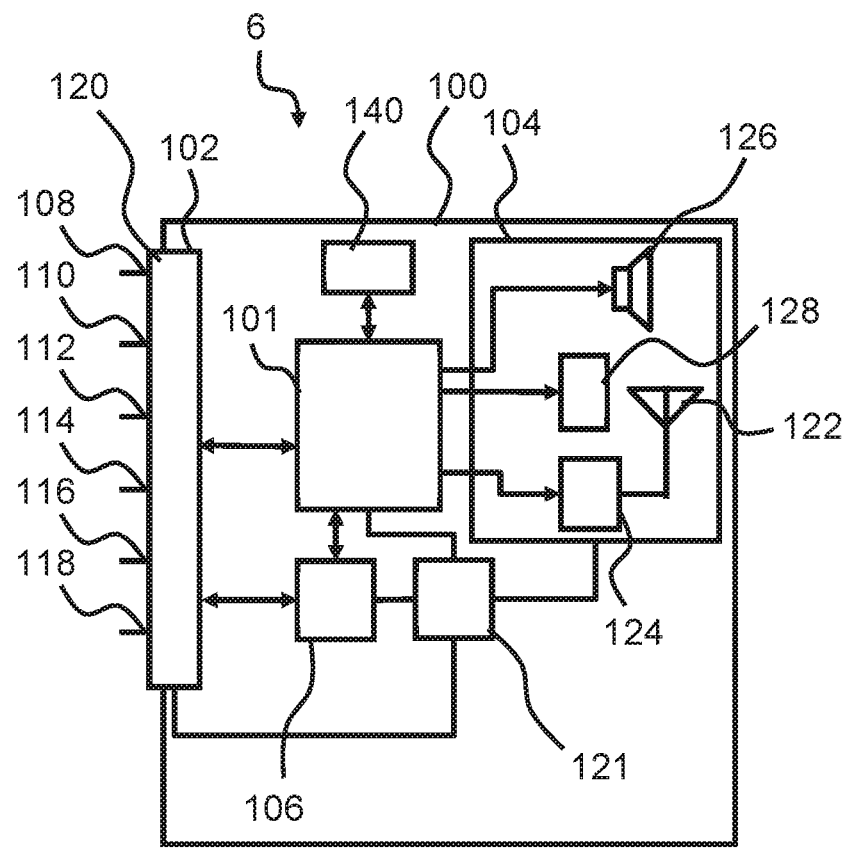
FIG. 2 illustrates an exemplary monitor device of the ostomy system.

FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101. For example, the sensor unit 140 comprises a temperature sensor for feeding temperature data to the processor and/or a G-sensor or accelerometer for feeding acceleration data to the processor 101. Additionally or alternatively, the sensor unit 140 comprises a humidity sensor and/or an acoustic sensor. The sensor unit 140 may comprise alternative and/or additional sensors suitable and/or relevant to an ostomy system as described.

The processor 101 is configured to apply a processing scheme, and the first interface 102 is configured for collecting ostomy data from the base plate and/or the sensor assembly part coupled to the first interface, the ostomy data comprising first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate and/or the sensor assembly part of the ostomy appliance based on one or more, e.g. all, of the first parameter data, the second parameter data and the third parameter data, wherein the operating state is indicative of a degree of radial erosion of the base plate and/or the sensor assembly part and/or acute leakage risk for the ostomy appliance. The monitor device 6 is configured to, in accordance with a determination that the operating state is a first operating state, transmit a first monitor signal comprising monitor data indicative of the first operating state of the base plate and/or the sensor assembly part via the second interface; and in accordance with a determination that the operating state is a second operating state, transmit a second monitor signal comprising monitor data indicative of the second operating state of the base plate and/or the sensor assembly part via the second interface.

Figure 3:
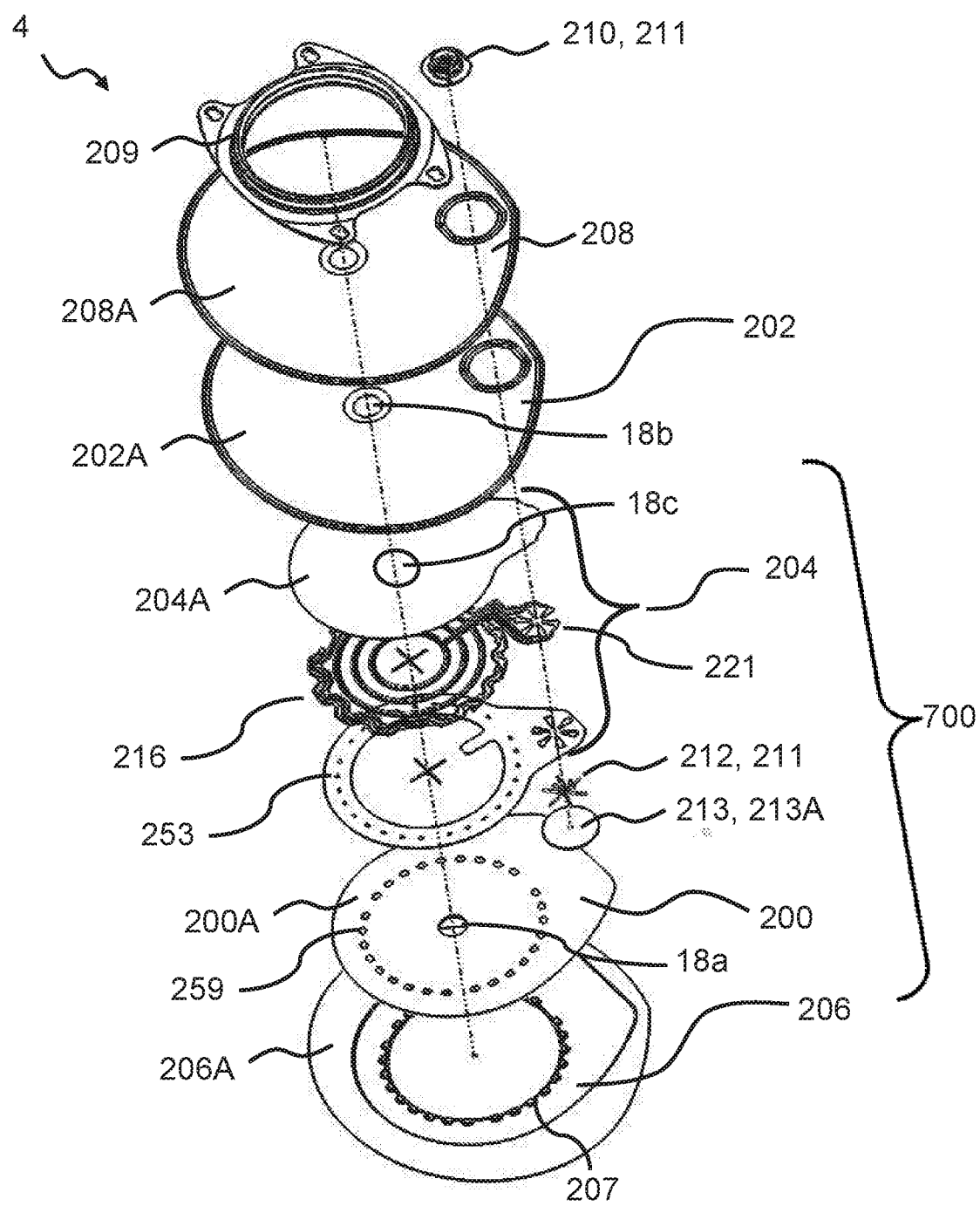
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

As illustrated in FIG. 3, the plurality of electrodes 216, which may be part of an electrode assembly 204 (see FIG. 4), may be arranged between the first and second adhesive layers 200, 202. Each of the first adhesive layer 200, second adhesive layer 202, and the electrode assembly 204 has a central opening 18a, 18b, 18c, respectively. The central openings 18a, 18b, 18c are aligned to define a central opening 18 (may also be denoted as the stoma-receiving opening) of the base plate 4. The central opening 18 is configured to fit around the stoma of the user. In embodiments, one or more of the central openings 18a, 18b, 18c may be absent, thus requiring the central missing opening(s) to be created before use (e.g. by the user).

In embodiments, the base plate 4 may comprise a top film 208 disposed distally to the second adhesive layer 202 and/or first adhesive layer 200. The top film 208 may provide protection to the rest of the base plate (e.g. except for the first connector 211 and the coupling ring 209) from being mechanically damaged (e.g. during handling and applying of the base plate 4) and/or chemically attacked (e.g. by the output, which may be acidic). A proximal surface 208B of the top film 208 may be coupled to a distal surface 202A of the second adhesive layer 202. In embodiments, a distal surface 208A of the top film 208 is substantially smooth thus prevents the base plate 4 from sticking to or damaging the clothing of the user.

According to embodiments, at least part of the base plate 4 may be one of bendable, flexible, twistable, and stretchable, e.g. to help improve coupling conformity and/or security of the adhesion between the base plate 4 and the surface of the subject.

In embodiments, the first and/or second adhesive layers 200, 202 comprise hydrocolloid (e.g. cellulose, alginate) and polymer matrix (e.g. SIS) materials such that the adhesive layers 200, 202 are both adhesive to the surface of the subject (e.g. skin of the patient) and moisture absorbent (e.g. absorbent of the moisture of sweat and output), e.g. in addition to being at least one of bendable, flexible, twistable, and stretchable.

In embodiments, the first adhesive layer 200 and the second adhesive layer 202 comprise adhesive materials adhesive to each other, enabling the two adhesive layers 200, 202 be adhered by pressing them together with or without heating. In embodiments, the adhesive strength to the surface of the user may be reduced with increasing moisture content in the first and second adhesive layers 200, 202, while the electrical conductivity increases with increasing moisture content in the first and second adhesive layers 200, 202.

In embodiments, the first adhesive layer 200 may have a smaller surface coverage than the second adhesive layer 202, while both the first and the second adhesive layers 200, 202 having bigger surface coverage than the plurality of electrodes 216 and the electrode assembly 204. Thereby, the plurality of electrodes 216 and the electrode assembly 204 may be encapsulated by adhesive, e.g. by the first adhesive layer 200 and the second adhesive layer 202.

For example, a proximal side 200B of the first adhesive layer 200 is configured to be attached to the skin of the patient and surround the stoma of the patient. The plurality of electrodes 216 of the electrode assembly 204, which may have a smaller surface coverage than the first adhesive layer 200, may be coupled to a distal side 200A of the first adhesive layer 200, leaving at least a rim portion of the distal surface 200A of the first adhesive layer 200 exposed. The second adhesive layer 202 may be distally coupled to the plurality of electrodes 216 or the electrode assembly 204 at a central region 400 (see FIG. 1) of the base plate 4. The second adhesive layer 202, which has larger surface coverage than the electrode assembly 204 and the plurality of electrodes 216, may further be distally coupled to the first adhesive layer 200 at least at the rim portion of the distal surface 200A of the first adhesive layer 200, leaving a rim portion of a proximal surface 202B of the second adhesive layer 202 exposed. The exposed rim of the proximal surface 202B of the second adhesive layer 202 may be configured to be attached to the skin of the patient at an outer region 404 (see FIG. 1) of the base plate 4 and surround the first adhesive layer 200. For example, the central region 400 of the base plate 4 may be substantially the same size as the electrode assembly 204 or the plurality of electrodes 216.

In embodiments, the difference in surface coverage between the first and second adhesive layers 200, 202 may be designed to feature the different adhesive properties of the first and second adhesive layers 200, 202. For example, the first adhesive layer 200 may possess higher moisture capacity and higher moisture absorbability than the second adhesive layer 202; whereas the second adhesive layer 202 may possess higher moisture permeability and higher adhesive strength to the surface of the subject than the first adhesive layer 202. In embodiments, adhesive properties of the first and second adhesive layers 200, 202 may be adjusted by adjusting the hydrocolloid-to-polymer compositional ratio. For example, increasing the hydrocolloid-to-polymer compositional ratio may increase moisture capacity and absorbability but may also decrease moisture permeability and adhesive strength to the surface of the subject.

In embodiments, the correlation between adhesive strength, moisture content, and electrical conductivity of the first adhesive layer 200 may be useful to how the ostomy system may be configured to detect and/or estimate moisture content in the first adhesive layer 200 by measuring electrical conductivity, by way of measuring resistances between the plurality of electrodes 216. Through the moisture content estimated and/or detected, the ostomy system may further provide information regarding whether the first adhesive layer 200 has detached from the skin of the patient. More detailed description on moisture and leakage of output sensing is provided in later paragraphs.

In embodiments, the first adhesive layer 200, being disposed between the plurality of electrodes 216 and the skin of the patient, may be designed to have a higher moisture capacity than, e.g. the second adhesive layer 202, e.g. to provide the ostomy system with a larger sensing range in moisture content. The first adhesive layer 200 may also possess a higher moisture absorbability than e.g. the second adhesive layer 202, e.g. to help increase sensing responsiveness to changes in moisture content near the stoma of the user, which would also effectively reduce problems such as skin irritation and swelling, as well as pre-mature detachment of the first adhesive layer 200 from the skin of the user.

In embodiments, the second adhesive layer 202, being configured to be coupled to the skin of the patient at the outer region 404 of the base plate 4 surrounding the first adhesive layer 200, may be designed to higher adhesive strength to the surface, e.g. skin, of the patient to reduce risk of detachment of the base plate 4 from the skin of the patient. This helps the base plate 4 to stay attached to the skin of the patient even when the first adhesive layer 200 has completely detached from the surface of the subject. This provides extra protection against leakage of output undesirably exiting the containment of the ostomy appliance, such as the base plate 4. The second adhesive layer 202 may be further designed to have the higher moisture permeability than e.g. the first adhesive layer 200, e.g. to help the absorbed moisture in the second adhesive layer 202 to exit the second adhesive layer 202 quicker, e.g. to maintain sufficiently high adhesive strength to the surface of the patient. This further enhances the attachment security of the base plate on the skin of the patient.

The release liner 206 may be releasably attached to the proximal surface 200A of the first adhesive layer 200 and configured to be peeled off (e.g. by the user) prior to applying the base plate 4 onto the skin. The release liner 206 may comprise a plurality of protrusions 207 arranged to extend through the first plurality of openings 259 of the first adhesive layer 200 when the release liner 206 is releasably attached to the proximal surface 200A of the first adhesive surface 200. The plurality of protrusions 207 helps retain the first plurality of openings 259 of the first adhesive layer 200 by inhibiting the adhesive material from creeping and closing the first plurality of openings 259. This may in particular be relevant when the first adhesive layer 200 have viscoelastic properties and/or have the tendency to deform plastically when stressed mechanically and/or heated.

In embodiments, the first adhesive layer 200 has a plurality of sensor point openings, which may be denoted as the first plurality of openings 259 of the first adhesive layer 200. The purpose of the sensor point opening is described in detail below (see e.g. FIG. 8).

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer 200. The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
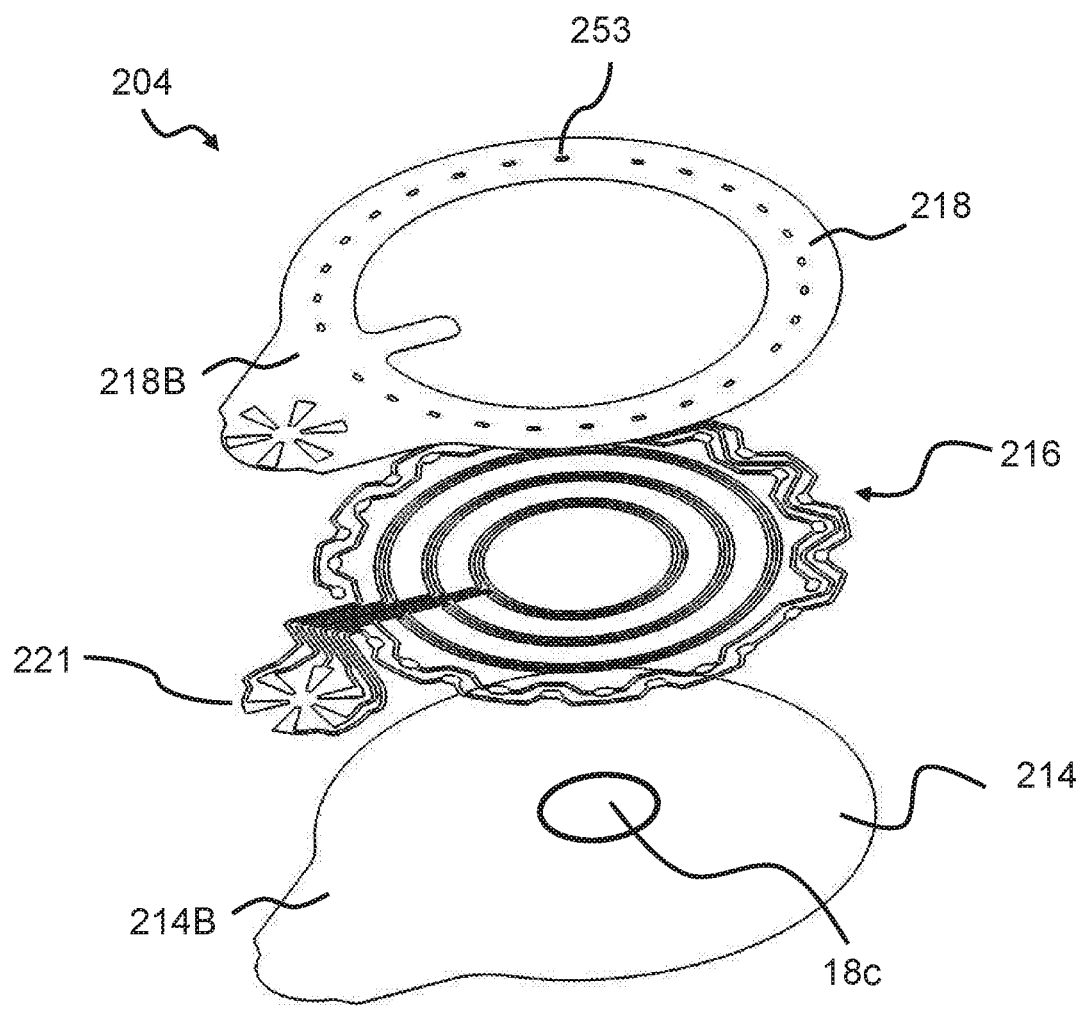
FIG. 4 is an exploded view of an exemplary electrode assembly.

FIG. 4 illustrates an exploded view of an exemplary electrode assembly 204 of a base plate and/or a sensor assembly part. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part for connecting the electrodes to respective terminal elements of the monitor interface. Further, electrode assembly 204 comprises a masking element 218 with proximal surface 218B and configured to insulate electrode parts of electrodes 216 from the first adhesive layer of the base plate and/or a sensor assembly part. The masking element 218 covers or overlaps with parts of the electrodes 216 when seen in the axial direction.

Figure 7:
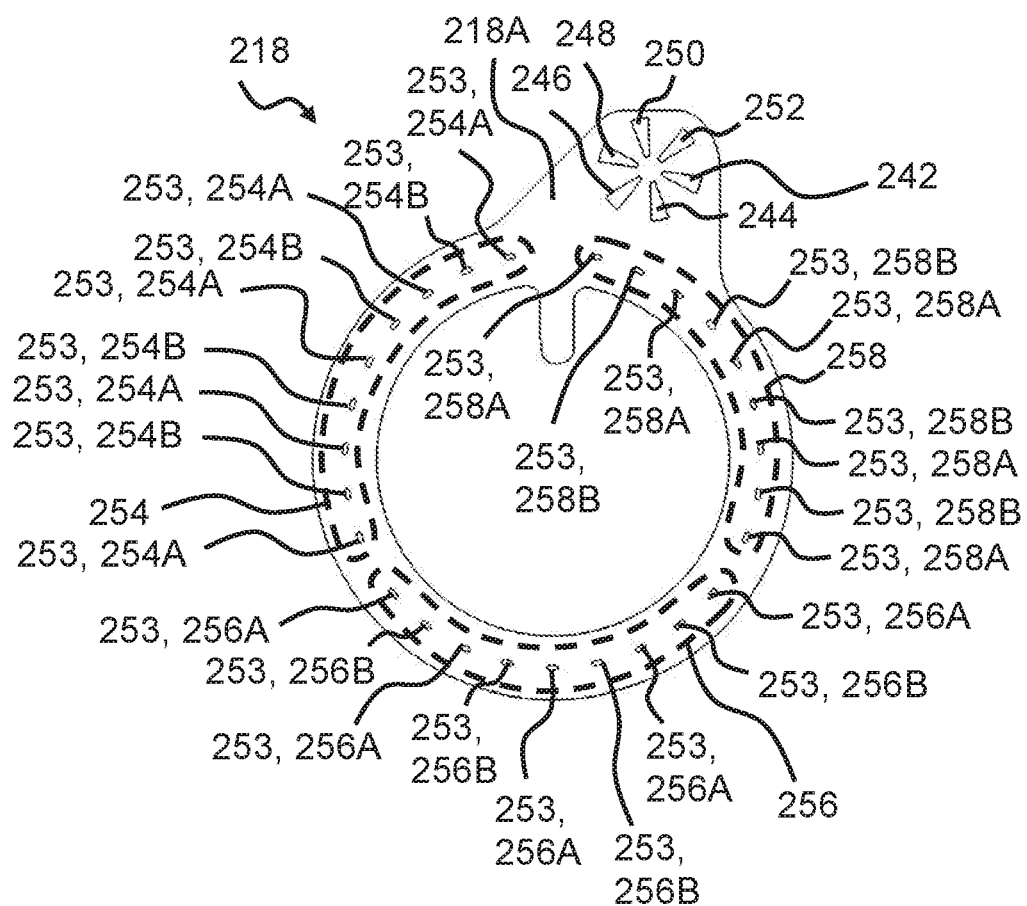
FIG. 7 is a distal view of an exemplary masking element.

As illustrated in FIG. 4, the masking element 218 may include a plurality of sensor point openings, which may also be denoted as a second plurality of openings 253 (see FIG. 7). Each of the second plurality of openings 253 may be arranged to expose a portion of one of the plurality of electrodes 216. The masking element 218 may also be configured to expose the connection parts 221 of the plurality of electrodes 216. The masking element 218 may shield the covered parts of the plurality of electrodes 216 from the first adhesive layer 200 and may have lower electrical conductivity than the first adhesive layer 200 to avoid creating a less resistive pathway (e.g. through the masking element 218) between any two of the plurality of electrodes 216 than through the first adhesive layer 200. This may improve the accuracy of correlating the measured resistance between any two of the plurality of electrodes 216 to the leakage of output.

In embodiments, the plurality of electrodes 216 may comprise at least one of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials. The masking element may comprise at least one of polymeric (e.g. polyurethane, PTFE, PVDF) and ceramic (e.g. alumina, silica) materials.

In embodiments, the plurality of electrodes 216 may be prepared by screen-printing, inkjet-printing, direct-ink-writing, pen-plotting, 3D-printing, fused-deposition-modelling, contact-transfer printing, spray painting, chemical vapour depositing, physical vapour depositing, atomic-layer-depositing, wire-bending, and any other methods known to a person skilled in the art. The plurality of electrodes 216 may further require one of heat-curing, UV-curing, and oxygen-activating.

Figure 5:
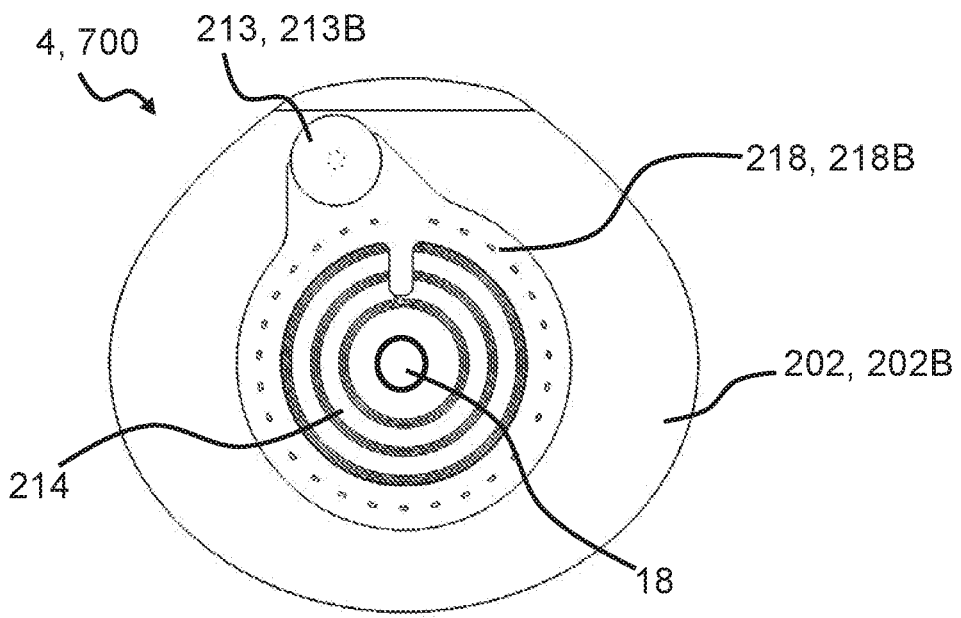
FIG. 5 is a proximal view of parts of a base plate and/or a sensor assembly part.

FIG. 5 is a proximal view of proximal surfaces of base plate parts of the base plate and/or a sensor assembly part without the first adhesive layer and the release liner. The base plate 4 and/or a sensor assembly part 700 comprises a first intermediate element 213 on the proximal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate and/or a sensor assembly part.

In embodiments, the first intermediate element 213 may prevent the plurality of terminals 212 of the monitor interface from contacting the first adhesive layer 200 (see FIG. 3). In embodiments, the first intermediate element 213 has an electrical conductivity lower than that of the first adhesive layer 200 to avoid creating a less resistive pathway (e.g. through the first intermediate element 213) than through the first adhesive layer 200 e.g. through the first adhesive layer at the one or more sensing zones 251 (see FIG. 11). Consequently, the connection parts 221 (see FIG. 4), shielded by the first intermediate element 213, may be non-responsive to the increased electrical conductivity of the first adhesive layer 200 when moisture has been absorbed. This helps to more accurately measure moisture content at the one or more sensing zones 251 (see FIG. 11) by the plurality of electrodes 216. The first intermediate element 213 may also strengthen the structural integrity of the base plate 4 at least near the connection parts 221.

Figure 6:
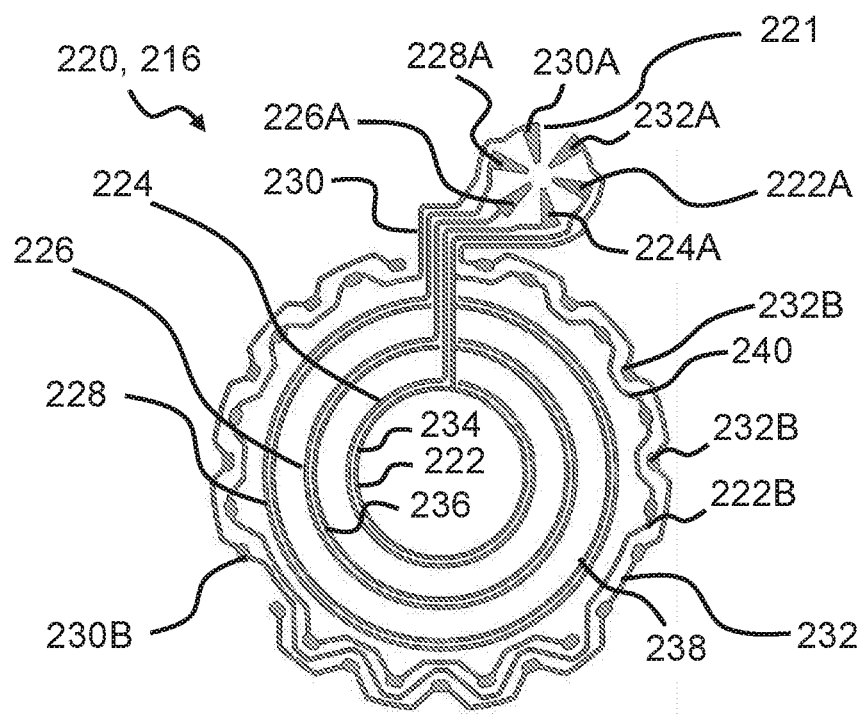
FIG. 6 is a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The electrodes 216 comprise connection parts 221. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprises a fifth connection part 232A.

The fourth electrode 230 comprises fourth sensing parts 230B. The fifth electrode 232 comprises fifth sensing parts 232B.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B.

The ground electrode 222, such as the fourth electrode part 240 and the fifth electrode part 232, forms a first leakage electrode. The fourth electrode 230 forms a second leakage electrode. The fifth electrode 232 forms a third leakage electrode.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings, which may be denoted as a second plurality of openings 253 of the masking element 218. The sensor point openings comprise primary sensor point openings shown within dotted line 254, each primary sensor point opening configured to overlap a part of a first leakage electrode, such as the ground electrode 222, and/or a part of a second leakage electrode, such as the fourth electrode 230. The primary sensor point openings 254 comprise, in the illustrated exemplary masking element, five primary first sensor point openings 254A each configured to overlap a part of the first leakage electrode, such as the ground electrode 222. The primary sensor point openings 254 comprise, in the illustrated exemplary masking element, four primary second sensor point openings 254B each configured to overlap a part of the second leakage electrode, such as the fourth electrode 230. The sensor point openings comprise secondary sensor point openings shown within dotted line 256, each secondary sensor point opening configured to overlap a part of the second leakage electrode, such as the fourth electrode 230, and/or a part of a third leakage electrode, such as the fifth electrode 232. The secondary sensor point openings 256 comprise, in the illustrated exemplary masking element, five secondary first sensor point openings 256A each configured to overlap a part of the third leakage electrode, such as the fifth electrode 232. The secondary sensor point openings 256 comprise, in the illustrated exemplary masking element, four secondary second sensor point openings 256B each configured to overlap a part of the second leakage electrode, such as the fourth electrode 230. The sensor point openings comprise tertiary sensor point openings shown within dotted line 258, each tertiary sensor opening configured to overlap a part of the third leakage electrode, such as the fifth electrode 232, and/or a part of the first leakage electrode, such as the ground electrode 222. The tertiary sensor point openings 258 comprise, in the illustrated exemplary masking element, five tertiary first sensor point openings 258A each configured to overlap a part of the third leakage electrode, such as the fifth electrode 232. The tertiary sensor point openings 258 comprise, in the illustrated exemplary masking element, four tertiary second sensor point openings 258B each configured to overlap a part of the first leakage electrode, such as the ground electrode 222.

Figure 8:
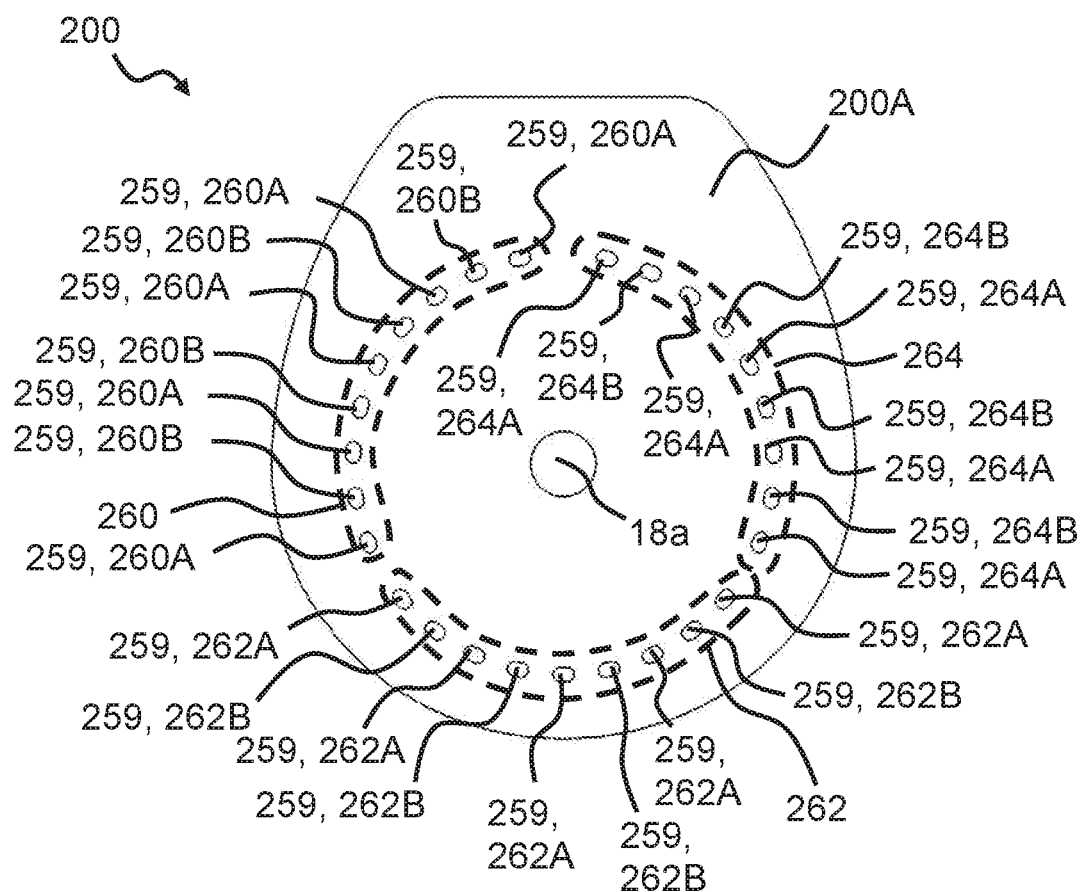
FIG. 8 is a distal view of an exemplary first adhesive layer.
Figure 9:
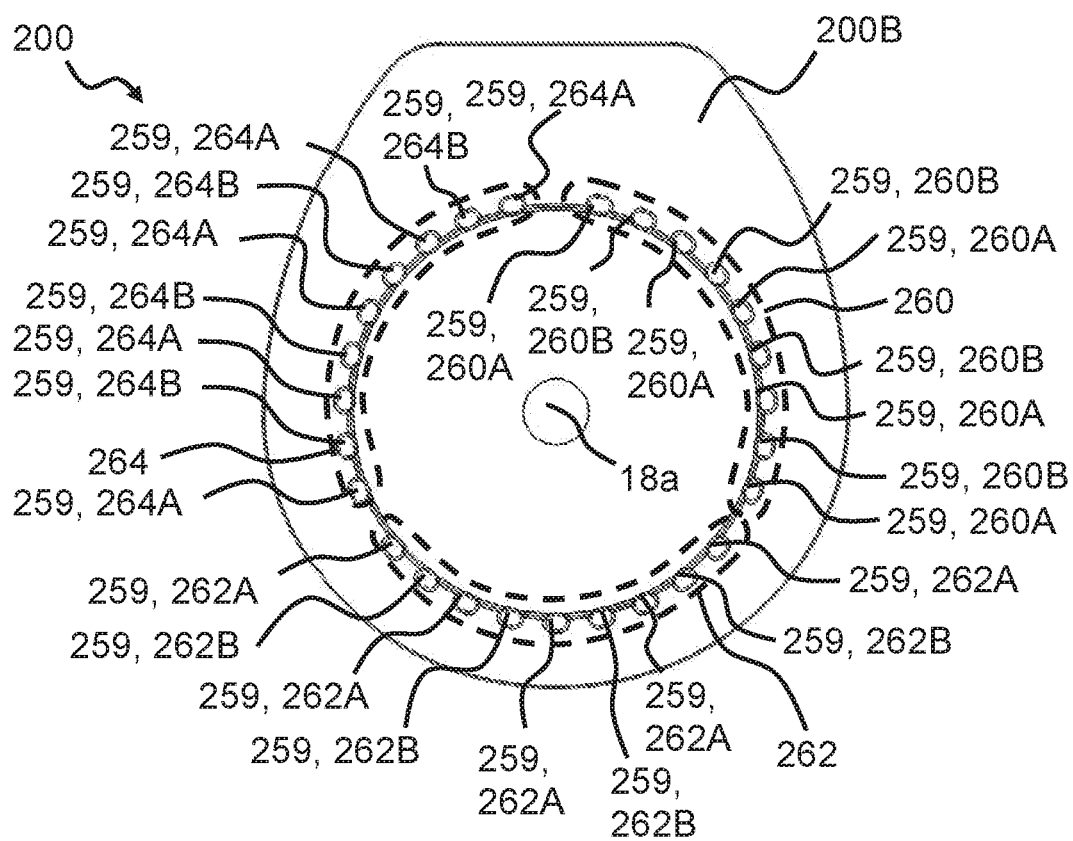
FIG. 9 is a proximal view of the first adhesive layer of FIG. 8.

FIG. 8 is a distal view of an exemplary first adhesive layer. The first adhesive layer 200 has a plurality of sensor point openings, which may be denoted as the first plurality of openings 259 of the first adhesive layer 200. The sensor point openings of the first adhesive layer comprise primary sensor point openings shown within dotted line 260, each primary sensor point opening configured to overlap a part of the first leakage electrode, such as the ground electrode 222, and/or a part of the second leakage electrode, such as the fourth electrode 230 of the electrode assembly. The primary sensor point openings 260 comprise, in the illustrated exemplary first adhesive layer, five primary first sensor point openings 260A each configured to overlap a part of the first leakage electrode, such as the ground electrode 222. The primary sensor point openings 260 comprise, in the illustrated exemplary first adhesive layer, four primary second sensor point openings 260B each configured to overlap a part of the second leakage electrode, such as the fourth electrode 230. The sensor point openings of the first adhesive layer comprise secondary sensor point openings shown within dotted line 262, each second sensor point opening configured to overlap a part of the second leakage electrode, such as the fourth electrode 230, and/or a part of the third leakage electrode, such as the fifth electrode 232 of the electrode assembly. The secondary sensor point openings 262 comprise, in the illustrated exemplary first adhesive layer, five secondary first sensor point openings 262A each configured to overlap a part of the third leakage electrode, such as the fifth electrode 232. The secondary sensor point openings 262 comprise, in the illustrated exemplary first adhesive layer, four secondary second sensor point openings 262B each configured to overlap a part of the second leakage electrode, such as the fourth electrode 230. The sensor point openings of the first adhesive layer comprise tertiary sensor point openings shown within dotted line 264, each tertiary sensor point opening configured to overlap a part of the third leakage electrode, such as the fifth electrode 232, and/or a part of the first leakage electrode, such as the ground electrode 222 of the electrode assembly. The tertiary sensor point openings 264 comprise, in the illustrated exemplary first adhesive layer, five tertiary first sensor point openings 264A each configured to overlap a part of the third leakage electrode, such as the fifth electrode 232. The tertiary sensor point openings 264 comprise, in the illustrated exemplary first adhesive layer, four tertiary second sensor point openings 264B each configured to overlap a part of the first leakage electrode, such as the ground electrode 222. FIG. 9 is a proximal view of the first adhesive layer of FIG. 8.

Figure 10:
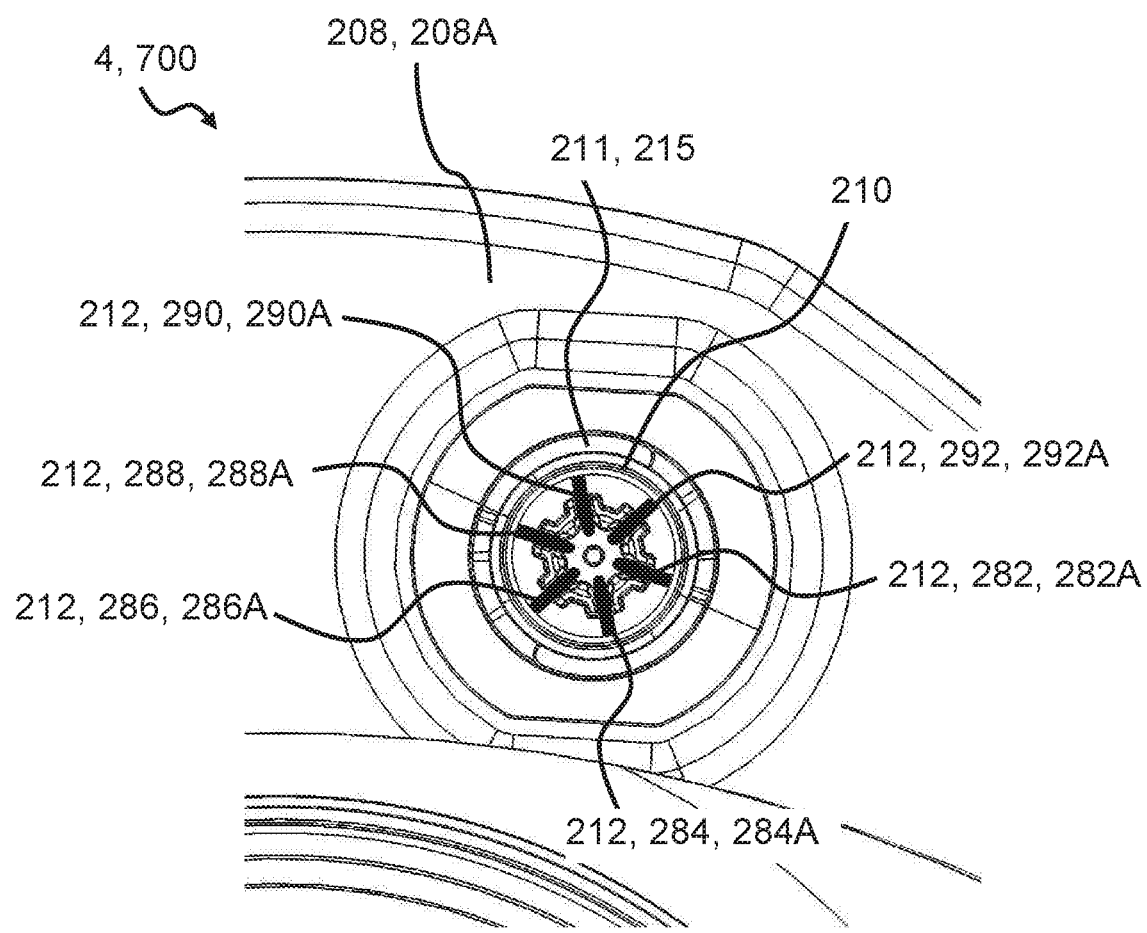
FIG. 10 is a distal view of a part of the base plate and/or a sensor assembly part including a monitor interface.

FIG. 10 is a more detailed distal view of a part of the base plate 4 and/or the sensor assembly part 700. The base plate 4 and/or the sensor assembly part 700 comprises a monitor interface. The monitor interface comprises the first connector 211. The first connector 211 comprises coupling part 210 configured to releasably couple the monitor device to the base plate and thus forming a releasable coupling. The first connector 211 of the monitor interface comprises a plurality of terminals formed by respective terminal elements for forming respective electrical connections with respective terminals of the monitor device.

The plurality of terminals of the first connector 211 of the monitor interface comprises a ground terminal element 282 forming a ground terminal 282A, a first terminal element 284 forming a first terminal 284, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate and/or the sensor assembly part, the number of terminals and the position of the terminals in the coupling part may be adapted to the electrode configuration used in the electrode assembly of the base plate and/or the sensor assembly part.

In reference to FIG. 1, FIG. 3, FIG. 6, and FIG. 10, the monitor interface 215 may include a plurality of terminals 212 and a coupling part 210. The plurality of terminals 212 may be configured to electrically couple the plurality of connection parts 221 of the plurality of electrodes 216 to the monitor device 6. The coupling part 210 may be configured to releasably and structurally couple the base plate 4 to the monitor device 6.

In reference to FIG. 3 and FIG. 10, the coupling part 210 may be distally attached or coupled to the top film 208, which may be distally coupled to the first and/or second adhesive layers 200, 202 as described previously. The coupling between the coupling part 210 and the top film 208 may be achieved by means including but not limited to: heat-bonding, mechanical fastening, solvent-bonding, UV-bonding, adhesive bonding, and/or ultrasonic welding.

Figure 11:
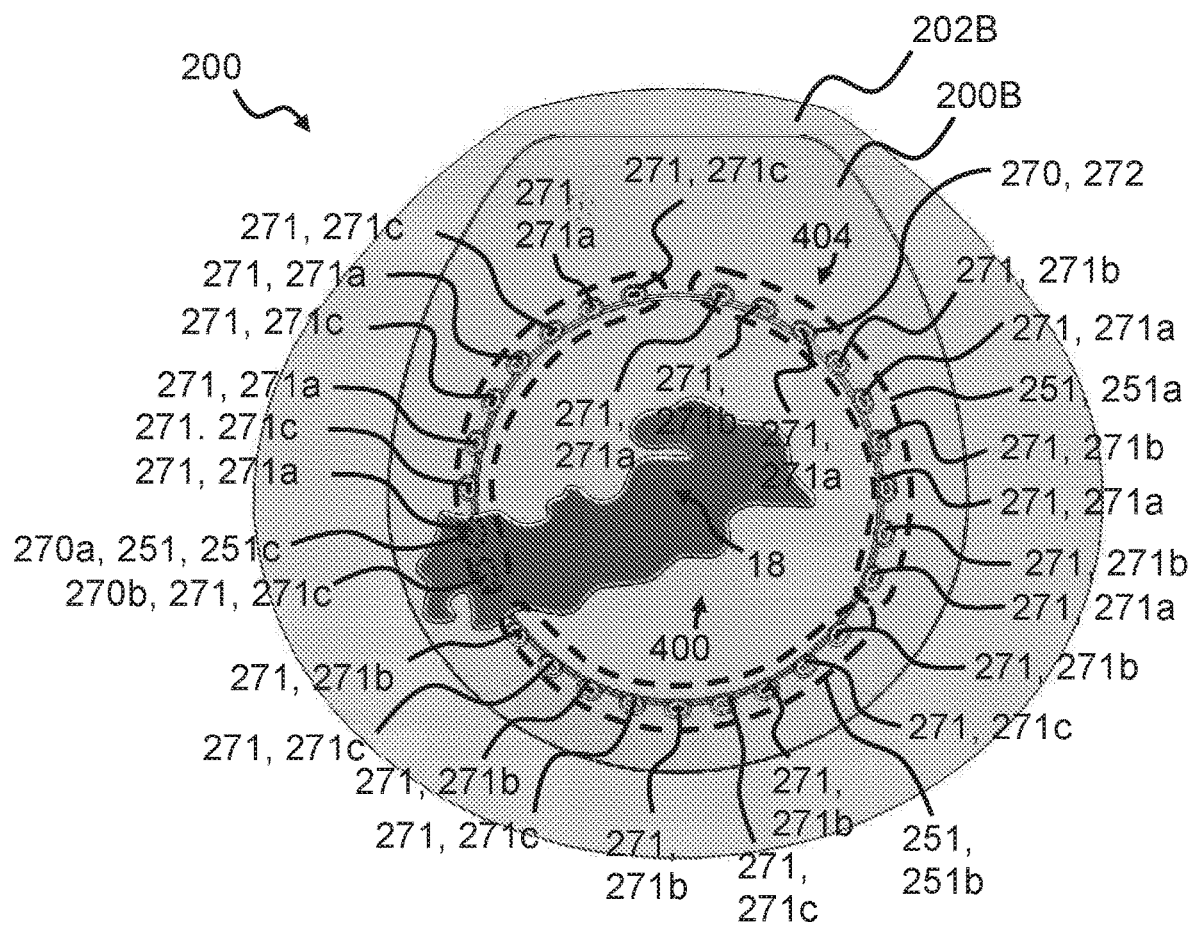
FIG. 11 is a proximal view of an exemplary base plate showing the leakage of output.
Figure 15:
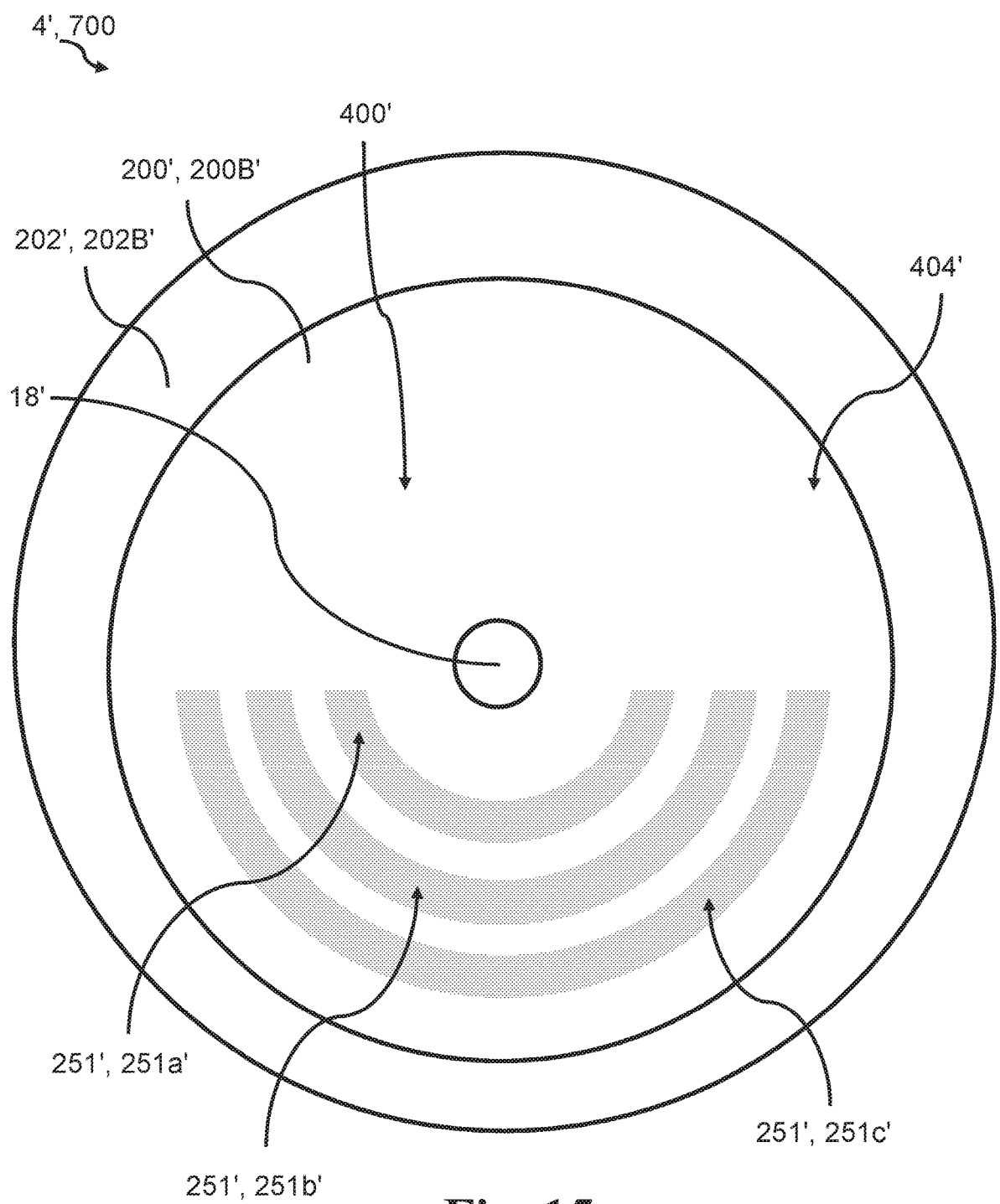
FIG. 15 illustrates sensing zones arranged radially.
Figure 16:
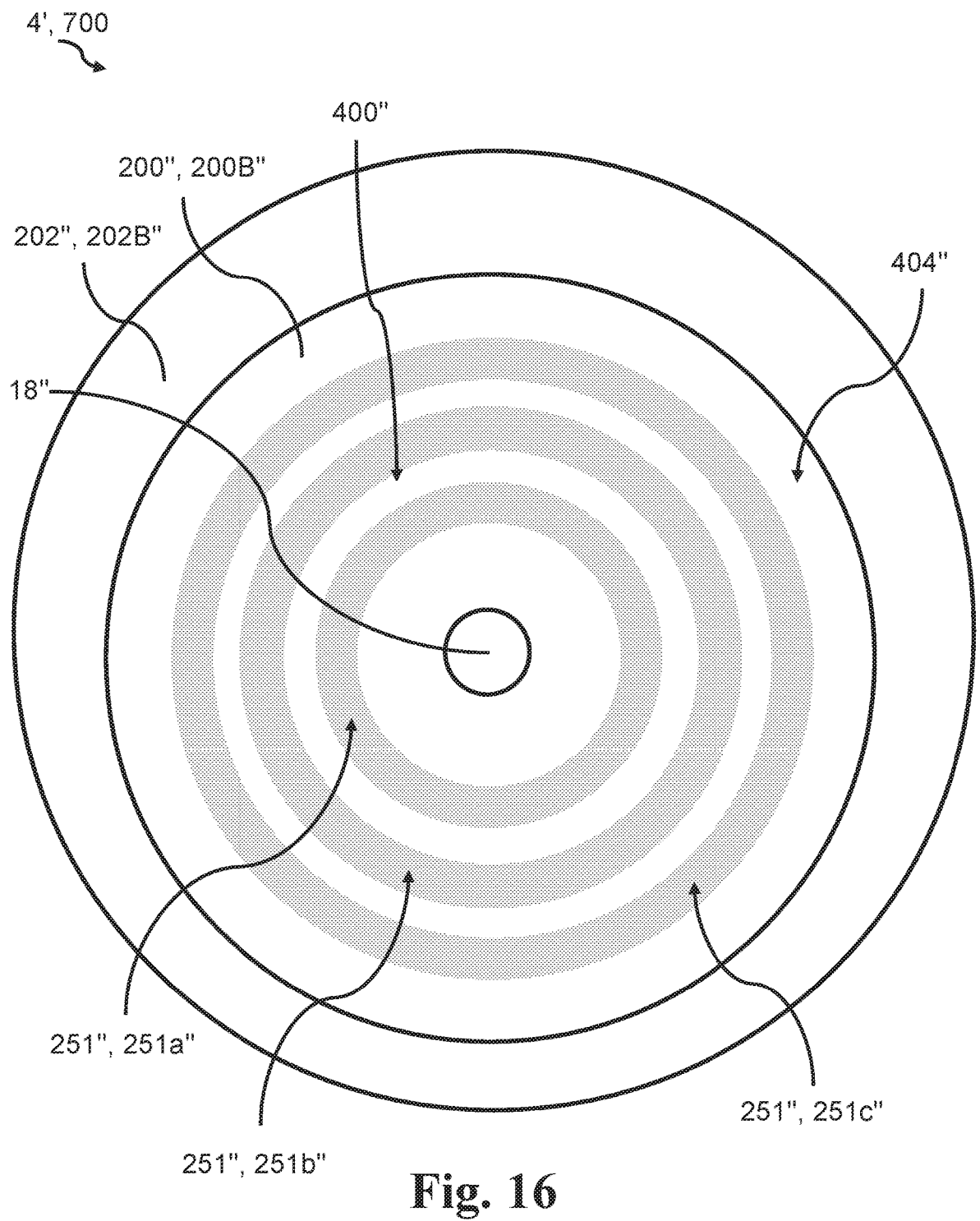
FIG. 16 illustrates sensing zones arranged concentrically.

FIG. 11 is a proximal view of an exemplary base plate 4 showing the leakage of output 18. In embodiments, the base plate 4 and/or the sensor assembly part 700 may comprise one or more sensing zones 251 distributed angularly about the central region 400 of the base plate 4 and/or the sensor assembly part 700, as illustrated in FIG. 11 with three sensing zones 251. Alternatively or additionally, the one or more sensing zones 251 may be distributed radially from the central region 400 of the base plate 4 and/or the sensor assembly part 700, as illustrated in FIG. 15, and/or concentrically about the central region 400 of the base plate 4 and/or the sensor assembly part, as illustrated in FIG. 16.

The ostomy system 1 (FIG. 1) may be configured to detect the moisture content within the first adhesive layer 200 at each of the one or more sensing zones 251. In embodiments, the moisture content is detected by measuring a resistance at each of the one or more sensing zones 251 across two of the plurality of electrodes 216 (see FIG. 6) in each of the one or more sensing zones 251. As will be described in greater detail, the ostomy system 1 may further be configured to detect the leakage of output, such as one or more indications of the leakage of output, at each of the one or more sensing zones 251 based on the resistance measured.

In embodiments, the angular distribution of the one or more sensing zones 251 helps the ostomy system 1 detect the leakage of output propagating from the central region 400 of the base plate 4 and/or the sensor assembly part 700 towards the outer region 404 of the base plate 4 and/or the sensor assembly part 700 in any direction within a base plane defined by the proximal surface 200B of the first adhesive layer 200. For example, as illustrated in FIG. 11, a first sensing zone 251a of the one or more sensing zones 251 may be disposed on a circle from 0 to 120 degrees about the central opening 18 of the base plate 4 and/or the sensor assembly part 700. Similarly, a second sensing zone 251b of the one or more sensing zones 251 may be disposed on the circle from 120 degrees to 240 degrees about the central opening 18 of the base plate 4 and/or the sensor assembly part 700. Similarly, a third sensing zone 251c of the one or more sensing zones 251 may be disposed on the circle from 240 to 360 degrees about the central opening 18 of the base plate 4 and/or the sensor assembly part 700.

Additionally or alternatively, the one or more sensing zones 251 may be distributed radially (see FIG. 15) from the central region 400 of the base plate 4 and/or the sensor assembly part 700 to help detect the propagation of the leakage of output from the central region 400 towards the outer region 404 of the base plate 4 and/or the sensor assembly part 700. Additionally or alternatively, the one or more sensing zones 251 may be distributed concentrically about (see FIG. 16) the central region 400 of the base plate 4 and/or the sensor assembly part 700 to help detect the propagation of the leakage of output from the central region 400 towards the outer region 404 of the base plate 4 and/or the sensor assembly part 700 in any direction.

As will be described in greater detail, the known locations of the one or more sensing zones 251 may further be used by the ostomy system 1, such as by the monitor device of the ostomy system, in determining a propagation direction and a propagation velocity of the leakage of output.

As illustrated in FIG. 11, the base plate 4 and/or the sensor assembly part 700 may comprise a plurality of sensor points 270, wherein a part of one of the plurality of electrodes 216 is exposed (e.g. not covered by the masking element 218 nor by the first adhesive layer 200) at each of the plurality of sensor points. As will be described in more detail, the ostomy system 1 may be configured to detect the leakage of output, such as one or more indications of the leakage of output, using the plurality of sensor points. For example, when the leakage of output has propagated far enough from the central region to reach a first sensor point 270a and a second sensor point 270b of the plurality of sensor points 270, as illustrated by FIG. 11, the ostomy system 1 may be configured to determine the leakage of output has entered the first sensing zone 251a where the first and second sensor points 270a, 270b are located.

Figure 12:
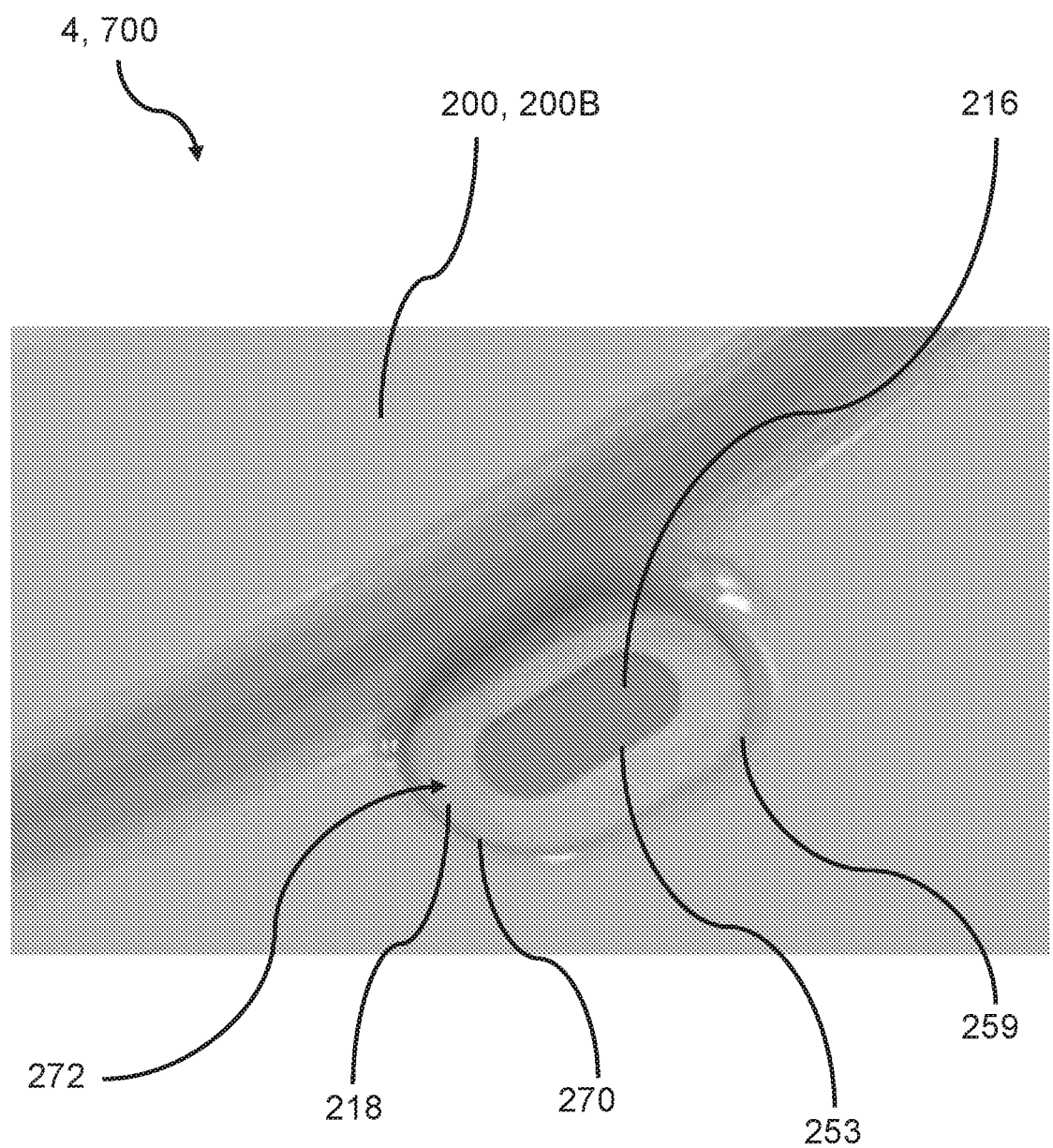
FIG. 12 is a proximal view of an exemplary base plate including a sensor point.

FIG. 12 is a proximal view of an exemplary base plate 4 and/or sensor assembly part 700 including a sensor point 270, such as a sensor point of the plurality of sensor points as described, e.g. in relation to FIG. 11. The proximal surface 200B of the first adhesive layer 200 may be configured to be in contact with the skin of the user when the base plate 4 and/or the sensor assembly part 700 is in use. As illustrated, the sensor point 270 is defined by an opening 259 of the first plurality of openings of the first adhesive layer 200 aligned with an opening 253 of the second plurality of openings of the masking element. In reference to previous figures, each of the plurality of sensor points 270 is defined by one of the first plurality of openings 259 (FIG. 8) of the first adhesive layer 200 aligning with one of the second plurality of openings 253 (FIG. 7) of the masking element 218 to expose a portion of one of the plurality of electrodes 216. The aligned first and second plurality of openings 253, 259 together define a plurality of conduits, such as sensor point openings, 272 (e.g. open channels from the skin to the plurality of electrodes 216) configured for the leakage of output to enter and contact the exposed parts of the plurality of electrodes 216. Thereby, the skin is unlikely to contact the electrodes, whereas output or other liquid may propagate through the sensor point openings 272 and provide a sensor reading through a short-circuiting event.

In reference to FIG. 11, the plurality of sensor points 270 may comprise a plurality of sensor point groups 271 including primary sensor points 271a, secondary sensor points 271b, and tertiary sensor points 271c. Each of the primary sensor points 271a includes an exposed portion of the ground electrode 222 of the plurality of electrodes 216 (see FIG. 6). In reference to FIG. 6 and FIG. 11, each of the secondary sensor points 271b includes an exposed portion of the fourth electrode 230 of the plurality of electrodes 216. Each of the tertiary sensor points 271c includes an exposed portion of a fifth electrode 232 of the plurality of electrodes 216. As illustrated in FIG. 11, the plurality of sensor points 270 are distributed alternatingly so that the nearest sensor point from a primary sensor point 271a, such as any of the primary sensor points 271a, is a secondary sensor point 271b or a tertiary sensor point 271c. The nearest sensor point from a primary sensor point 271a may not be another of the primary sensor points 271a. In such arrangement, any two of the plurality of sensor points 270 neighboring each other would expose two of the plurality of electrodes 216, which facilitates the detection of the leakage of output, such as one or more indications of the leakage of output.

Similar to the angular distribution of the one or more sensing zones 251, as exemplified in FIG. 11, the plurality of sensor points 270 may be distributed angularly about the central region 400 of the base plate 4 and/or the sensor assembly part 700 to help detect the leakage of output propagating from the central region 400 of the base plate 4 and/or the sensor assembly part 700 outwards towards the outer region 404 of the base plate 4 and/or the sensor assembly part 700, e.g. in any direction within the base plane. Additionally or alternatively, the plurality of sensor points 270 and/or sensing zones 251 may be distributed radially (FIG. 15) from the central region 400 of the base plate 4 and/or the sensor assembly part 700 to help detect the propagation of the leakage of output from the central region 400 towards the outer region 404 of the base plate 4 and/or the sensor assembly part 700. Additionally or alternatively, the plurality of sensor points 270 and/or sensing zones 251 may be distributed concentrically (FIG. 16) about the central region 400 of the base plate 4 and/or the sensor assembly part 700 to help detect the propagation of the leakage of output from the central region 400 towards the outer region 404 of the base plate 4 and/or the sensor assembly part 700, e.g. in any direction.

In embodiments, each of the one or more sensing zones 251 includes at least sensing parts, e.g. 222B, 230B, 232B, (see FIG. 6) of two of the plurality of electrodes 216 such that each of the one or more sensing zones 251 may be generally defined, outlined, designated, and/or specified by two of the plurality of electrodes 216. For example, the ground and fourth of the plurality of electrodes 222, 230 may define the first sensing zone 251a, the fourth electrode 230 and the fifth electrode 232 of the plurality of electrodes 216 may define the second sensing zone 251b, and the ground electrode 222 and the fifth electrode 232 of the plurality of electrodes 216 may define the third sensing zone 251c. The ground electrode 222 forms a first leakage electrode. The fourth electrode 230 forms a second leakage electrode. The fifth electrode 232 forms a third leakage electrode. In embodiments, at least one of the plurality of electrodes 216 may be in more than one of the one or more sensing zones 251 (e.g. the ground electrode 222). In addition to the first, second, and third sensing zones 251a, 251b, and 251c, a sixth electrode, e.g. forming a fourth leakage electrode, of the plurality of electrodes may form a fourth, fifth, and sixth sensing zones with the ground, fourth, and/or fifth electrodes 222, 230, 232. In embodiments, three or more of the plurality of electrodes 216 may be in one of the one or more sensing zone 251 such that two or more resistances are measured across any two of the three or more of the plurality of electrodes 216, which in combination indicate the moisture content in the corresponding sensing zone 251.

In embodiments, each of the one or more sensing zones 251 includes at least sensing parts of two of the plurality of sensor point groups 271, wherein each of the two of the plurality of sensor point groups 271 exposes portions of one of the plurality of electrodes 216. For example, the first sensing zone 251a may comprise some of the primary sensor points 271a and some of the secondary sensor points 271b. The second sensing zone 251b may comprise some of the secondary sensor points 271b and some of the tertiary sensor points 271c. The third sensing zone 251c may comprise some of the primary sensor points 271a and some of the tertiary sensor points 271c.

As described previously, the ostomy system 1 may be configured to, by measuring resistances across the plurality of electrodes 216, detect leakage of output present in the base plane, such as one or more indications of the leakage of output present in the base plane. In embodiments, such detection of leakage of output and/or indication(s) of leakage of output may be in the form of detection a short-circuit event.

Figure 13:
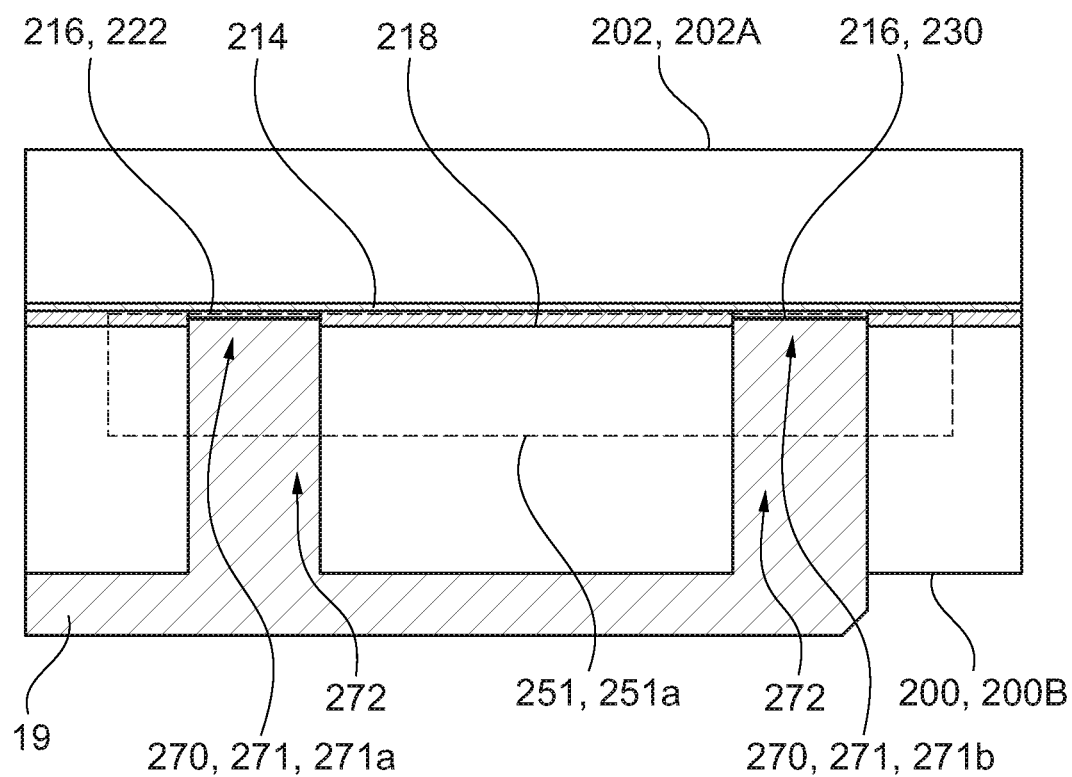
FIG. 13 is a cross-sectional view of an exemplary base plate of the ostomy system.

FIG. 13 is a cross-sectional view of an exemplary base plate 4 and/or the sensor assembly part 700 (as illustrated in FIG. 11) of the ostomy system 1. In embodiments, the ostomy system 1 may be configured to detect a short-circuit event when the leakage of output connects one sensor point of one of the plurality of sensor groups 271 with one sensor point of another plurality of sensor groups 271. During such short-circuit event, the leakage of output 19 may contact one of the plurality of electrodes 216 by entering one of the plurality of sensor point openings 272 and contact another of the plurality of electrodes 216 by entering another of the plurality of sensor point openings 272. In embodiments, the first adhesive layer 200 may be designed to have a lower electrical conductivity than that of the output, such that the output would create a less resistive pathway between the two electrodes compared to a pathway through the first adhesive layer 200.

For example, the ostomy system 1 may be configured to detect a short-circuit event in the first sensing zone 251a when the leakage of output 19 connects or bridges the ground electrode 222 and the fourth electrode 230 in the first sensing zone—by way of entering one of the plurality of sensor point openings 272 exposing a portion of the ground electrode 222 at one of the primary sensor points 271a and entering another of the plurality of sensor point openings 272 exposing a portion of the fourth electrode 230 at one of the secondary sensor points 271b. The output 19 connecting the ground and fourth electrodes 202, 220 would create a less resistive pathway than a pathway through the first adhesive layer 200.

Similarly, the ostomy system 1 may detect a short-circuit event at any of the one or more sensing zones indicative that the leakage of output has entered the corresponding sensing zone. This may be of importance due to the presence of output between the first adhesive layer 200 of the base plate and/or the sensor assembly part and the skin of the patient would indicate that the first adhesive layer 200 may no longer adhere (i.e. detached) to the skin of the patient. A detached first adhesive layer 200 greatly increases the risk of leakage of output exiting the containment of the ostomy appliance.

In embodiments, the first adhesive layer 200 is at least slightly air permeable to help the leakage of output enter the plurality of sensor point openings 272 at the plurality of sensor points 270 with minimal resistive pressures created by the leakage of output compressing the air in the plurality of sensor point openings 272. In embodiments, the plurality of sensor point openings 272 is configured for the leakage of output to easily enter such that the ostomy system 1 may detect the short-circuit event and register the leakage signal less than 1 second from the leakage of output entering the corresponding sensing zone.

Figure 14:
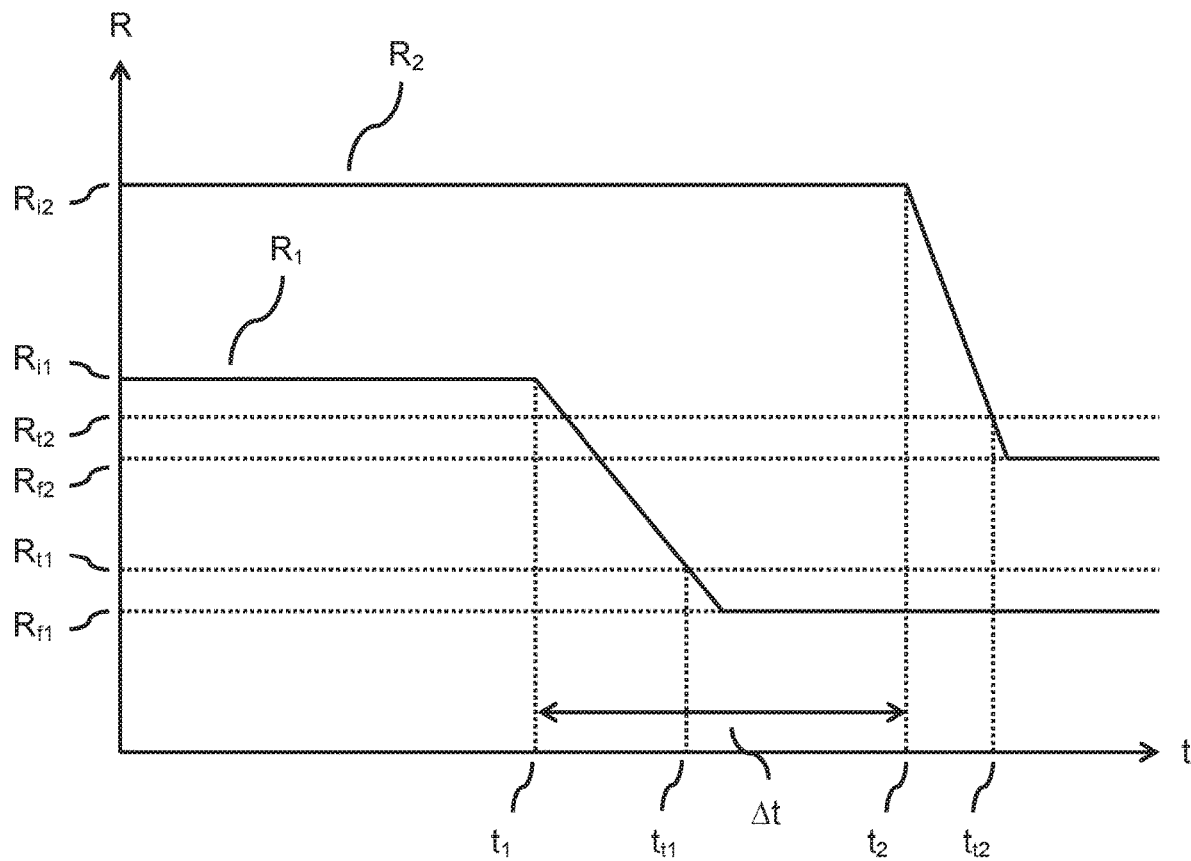
FIG. 14 illustrates an exemplary resistance measurement.

FIG. 14 is a diagram illustrating exemplary resistance measurements.

A first resistance $R_1$ is measured in a first sensing zone. The first resistance $R_1$ may be measured between a ground electrode and a fourth electrode, e.g. a first leakage electrode and a second leakage electrode, of the plurality of electrodes, wherein the ground and fourth electrodes have exposed parts in the first sensing zone. As shown, the first resistance $R_1$ measured in the first sensing zone, before a short-circuit event, substantially equals to a first primary resistance value $R_{i1}$ The first primary resistance value $R_{i1}$ has a relatively high value and represents the relatively high electrical resistivity of the first adhesive layer and/or the masking layer between the two electrodes used by the monitor device of the ostomy system (FIG. 1) for resistance measurement at the first sensing zone. As illustrated in FIG. 14, the first resistance $R_1$ starts to drop from the first primary resistance value $R_{i1}$ to about a first secondary resistance value $R_{f1}$ when a short-circuit event occurred at time $t_1$. The first secondary resistance value $R_{f1}$ has a relatively low value and represents the relatively low electrical resistivity of the output, which has connected the two electrodes used for the resistance measurement in the first sensing zone.

A second resistance $R_2$ is measured in a second sensing zone. The second resistance $R_2$ may be measured between the fourth electrode and a fifth electrode, e.g. the second leakage electrode and a third leakage electrode, of the plurality of electrodes, wherein the fourth and fifth electrode have exposed parts in the second sensing zone. As shown, the second resistance $R_2$ measured in the second sensing zone, before a short-circuit event, substantially equals to a second primary resistance value $R_{i2}$. The second primary resistance value $R_{i2}$ has a relatively high value and represents the relatively high electrical resistivity of the first adhesive layer and/or the masking layer between the two electrodes used by the monitor device of the ostomy system 1 (FIG. 1) for resistance measurement of the second sensing zone. As illustrated in FIG. 14, the second resistance $R_2$ starts to drop from the second primary resistance value $R_{i2}$ to about a second secondary resistance value $R_{f2}$ when a short-circuit event occurred at time $t_2$. The second secondary resistance value $R_{f2}$ has a relatively low value and represents the relatively low electrical resistivity of the output, which has connected the two electrodes used for the resistance measurement in the second sensing zone.

The monitor device 6 of the ostomy system 1 may be configured to generate a leakage signal when a measured resistance, e.g. $R_1$ and/or $R_2$ drops below a trigger resistance value, e.g. $R_{t1}$ and/or $R_{t2}$, e.g. at time $t_{r1}$ and/or $t_{r2}$, respectively, to indicate that a short-circuit event has occurred in the corresponding sensing zone. In embodiments, different threshold values may be employed for different sensing zones, e.g. to reflect different electrode characteristics such as electrode length and/or inter-electrode spacing.

In embodiments, the ostomy system is configured to detect leakage of output propagating from the central opening 18 of the base plate and/or the sensor assembly part towards the outer region 404 of the base plate 4 and/or the sensor assembly part. Thus in addition to detecting short-circuit events at the one or more sensing zones; the monitor device 6 of the ostomy system 1 may be configured to generate leakage signals. A leakage signal may comprise at least one of leakage location, leakage propagating direction, and leakage propagating velocity. The leakage location may comprise the sensing zones where short-circuit events have been detected. Additionally, the leakage location may comprise a region between the sensing zones where short-circuit events have been detected.

In reference to FIG. 14, the first derivative (slope) of the resistance drop as a function of time, e.g. the rate of change of the resistance, may be correlated to the influx of moisture in the respective sensing zones. Additionally, the slope may provide information as to the quantity of moisture entering the corresponding sensing zone. Furthermore, the rate of change may be indicative of whether the underlying cause of the detected increased moisture content. For example, a big rate of change may be indicative of output causing the moisture increase, while a smaller rate of change may be indicative of sweat causing the moisture increase.

FIG. 15 and FIG. 16 each illustrates a base plate 4', 4" and/or a sensor assembly part with sensing zones arranged radially from (FIG. 15) and concentrically about (FIG. 16) the central opening 18', 18", such as the stomal opening, of the base plate 4', 4" and/or the sensor assembly part and outwards towards the outer region 404', 404" of the base plate 4', 4" and/or the sensor assembly part. When the sensing zones are in such arrangement, the leakage propagating direction may comprise a direction from one of the one or more sensing zones 251', 251" that first registered a short-circuit event, to another of the one or more sensing zones 251', 251" that next registered a short-circuit event. The leakage propagating direction may be substantially parallel to the base plate and/or the sensor assembly part and the base plane. The leakage propagating velocity may comprise a velocity derived by dividing the distance between the two sensing zones where short-circuit events have sequentially been detected, by a time-delay, e.g. At of FIG. 14, between the detection of short-circuit events at the two sensing zones (see FIG. 14).

In embodiments, the leakage propagating velocity derived may help the ostomy system 1 in determining a remaining usage time (e.g. time till replacement) of the base plate 4. For example, from the known locations of the sensing zones, the size of the first adhesive layer 200, adhesive properties (e.g. adhesive strength), and the derived leakage propagating velocity, the ostomy system 1 may be configured to determine the remaining time until the leakage of output spreads to substantial portions (or substantially near the outer region 404 of the base plate 4 and/or the sensor assembly part) of the first adhesive layer 200. The ostomy system 1 may be configured to provide warning to the user such that the base plate 4 may be replaced before the leakage of output exits the containment of the ostomy appliance 2 due to greatly reduced adhesive strength between the base plate 4 and/or the sensor assembly part and the skin of the user owing to the leakage of output. Such a prediction would help prevent unintended detachment of the base plate 4 and/or the sensor assembly part and may further reduce the time of contact between the output and the skin of the user by indicating that output is in contact with the skin and that the base plate 4 may be due for a replacement or cleaning. The described warning may reduce skin problems such as irritation or swelling that would result from the skin being in contact with output for extended period of time.

FIG. 15 also illustrates that the sensing zones may span a limited angle space, such as an angle space of, e.g., 180 degrees. In the illustrated example of FIG. 15, the three sensing zones span the same angle space. However, it is noted that in other embodiments the plurality of sensing zones may span different angle spaces, such as illustrated in FIG. 11.

Figure 17:
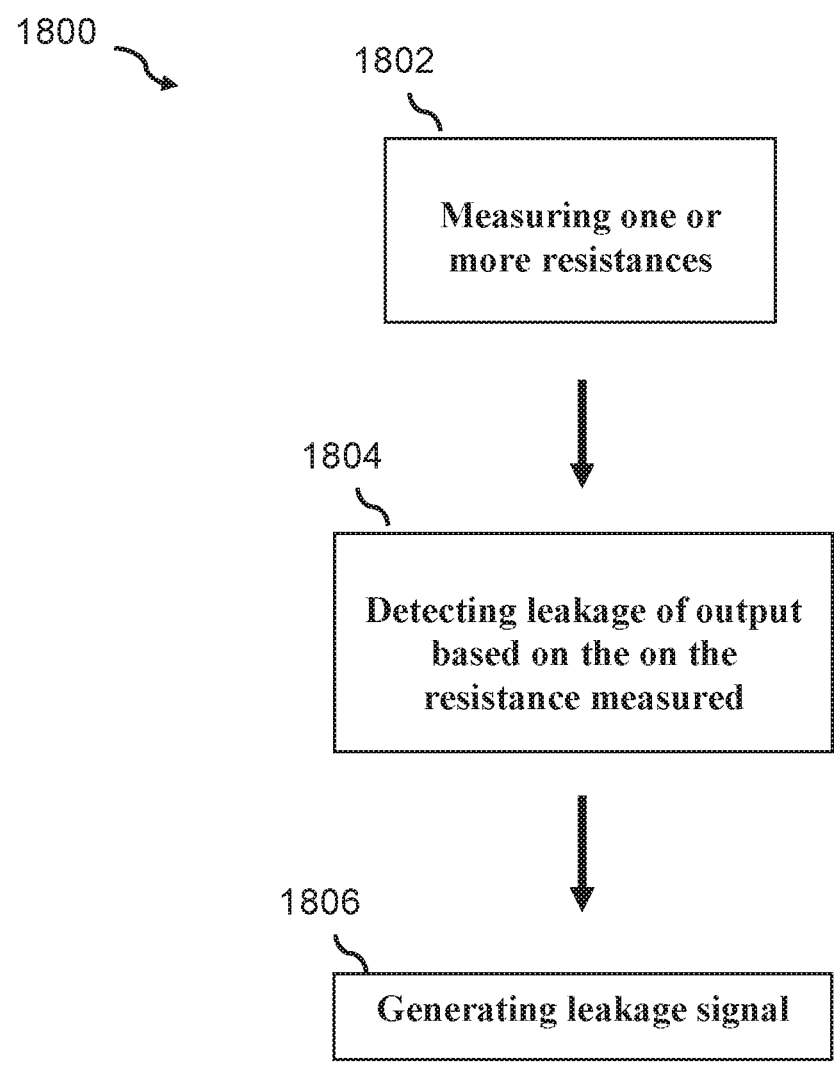
FIG. 17 depicts an illustrative method for detecting an indication of leakage of output.

FIG. 17 depicts an illustrative method 1800 for detecting a leakage of output, such as one or more indications of the leakage of output, between a base plate and/or the sensor assembly part and the surface of a subject, in accordance with embodiments. The method 1800 comprises measuring 1802 one or more resistances via a plurality of electrodes 216 of the base plate 4 and/or the sensor assembly part by a monitor device 6 of the ostomy system 1. Each of the one or more resistances is measured by two of the plurality of electrodes 216 at one of the one or more sensing zones 251.

The method 1800 may further comprise detecting 1804 the leakage of output, such as one or more indications of the leakage of output, in one or more sensing zones 251. Detecting 1804 may include comparing the measured resistance to an initial/baseline resistance for each of the one or more sensing zones 251. When the leakage of output is present in one of the one or more sensing zones 216, one of the one or more resistances measured 1802 at that sensing zone would decrease quickly. In embodiments, the detecting step 1804 comprises determining whether each of the one or more resistances measured is smaller or equal to one of the one or more threshold resistance values, wherein each of the one or more threshold resistance values are the electrical resistances measurable by the plurality of electrodes 216 in each of the one or more sensing zones 251 during a short-circuited event.

The method 1800 may further comprise generating 1806 a leakage signal when a leakage of output and/or one or more indications of the leakage of output has been detected in any of the one or more sensing zones 251. The leakage signal may comprise at least one of leakage location, leakage propagating direction, and leakage propagating velocity.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Embodiments of the present disclosure are set out in the following items:

1. An ostomy system configured to detect a leakage of output between a base plate and/or a sensor assembly part of the ostomy system and a surface of a subject, the ostomy system comprising:
   a base plate and/or a sensor assembly part including:
      a first adhesive layer having a distal surface, a proximal surface, and a first plurality of openings, and
      an electrode assembly disposed on the distal surface of the first adhesive layer, the electrode assembly including:
         a plurality of electrodes, and
         a masking element between the plurality of electrodes and the first adhesive layer, the masking element having a second plurality of openings aligned with the first plurality of openings of the first adhesive layer, each of the aligned first and second plurality of openings exposes a portion of one of the plurality of electrodes to define one of a plurality of sensor points; and
   a monitor device electrically coupled to the plurality of electrodes of the base plate and/or sensor assembly part, the monitor device being configured to (i) measure one or more resistances between the plurality of electrodes and (ii) detect the leakage of output based on the measured one or more resistances.
2. The ostomy system of item 1, wherein a first electrode and a second electrode of the plurality of electrodes are configured to short-circuit through the leakage of output when the leakage of output connects the first and second electrodes at a first sensor point and a second sensor point of the plurality of sensor points, one of a plurality of conduits exposing a portion of the first electrode at the first sensor point, and another of the plurality of conduits exposing a portion of the second electrode at the second sensor point.
3. The ostomy system of any of the preceding items, configured to detect, using the one or more resistances measured by the monitor device via the plurality of electrodes, the leakage of output propagating from a central region of the base plate and/or the sensor assembly part towards any direction in a base plane defined by the proximal surface of the first adhesive layer.
4. The ostomy system of any of the preceding items, wherein the base plate and/or the sensor assembly part comprises one or more sensing zones including a first sensing zone and a second sensing zone, each of the one or more sensing zones includes at least sensing parts of two of the plurality of electrodes.
5. The ostomy system of item 4, wherein at least some of the one or more sensing zones being distributed at least one of circularly about, radially from, and concentrically about a central opening of the base plate and/or the sensor assembly part.
6. The ostomy system of any of the preceding items, wherein the first adhesive layer has a first electrical conductivity, the masking element has a second electrical conductivity, and output has a third electrical conductivity, wherein the second electrical conductivity being lower than the first electrical conductivity, and the third electrical conductivity being higher than the first electrical conductivity.
7. The ostomy system of any of the preceding items, wherein the masking element comprises at least one of polymeric and ceramic materials.
8. The ostomy system of any of the preceding items, wherein the plurality of electrodes comprises at least one of metallic, ceramic, polymeric, and carbonaceous materials.
9. The ostomy system of any of the preceding items, wherein the plurality of electrodes comprises one of silver and carbon.
10. The ostomy system of any of the preceding items, wherein the base plate and/or the sensor assembly part is at least one of bendable, flexible, twistable, and stretchable.
11. The ostomy system of any of the preceding items, wherein the base plate and/or the sensor assembly part further comprises a second adhesive layer coupled distally to the first adhesive layer and the electrode assembly.
12. The ostomy system of item 11, wherein the second adhesive layer is at least one of more adhesive to the surface of the subject, more moisture permeable, less moisture-absorbent, and lower in moisture capacity than the first adhesive layer.
13. The ostomy system of any of the preceding items, wherein the base plate and/or the sensor assembly part further comprises a release liner releasably attached to the proximal surface of the first adhesive layer, the release liner having a plurality of protrusions configured to extend into the first plurality of openings of the first adhesive layer.
14. The ostomy system of any of the preceding items, wherein the base plate and/or the sensor assembly part further comprises a first intermediate element between the first adhesive layer and a plurality of connection parts of the plurality of electrodes.
15. The ostomy system of item 14, wherein the first intermediate element is less electrically conductive than the first adhesive layer.
16. The ostomy system of any of the preceding items, wherein the electrode assembly further comprises a support layer coupled to the plurality of electrodes.

17. The ostomy system of any of the preceding items, wherein the first adhesive layer comprises a hydrocolloid and a polymer matrix.
18. The ostomy system of any of the preceding items, wherein the monitor device is configured to generate a leakage signal when the leakage of output is detected in at least one of the one or more sensing zones.
19. A method of detecting a leakage of output between a base plate and/or a sensor assembly part of an ostomy system and a surface of a subject, the ostomy system including the base plate and/or the sensor assembly part and a monitor device, the base plate and/or the sensor assembly part comprising (i) a first adhesive layer having a distal surface, a proximal surface, and a first plurality of openings, and (ii) an electrode assembly comprising a plurality of electrodes and a masking element between the plurality of electrodes and the first adhesive layer, the masking element having a second plurality of openings aligned with the first plurality of openings of the first adhesive layer, each of the aligned first and second plurality of openings exposes a portion of one of the plurality of electrodes to define one of a plurality of sensor points, the monitor device electrically coupled to the plurality of electrodes of the base plate and/or the sensor assembly part, the method comprising:
    measuring, via the plurality of electrodes, one or more resistances, each of the one or more resistances measured between two of the plurality of electrodes; and
    detecting the leakage of output based on the measured one or more resistances.
20. The method of item 19, wherein measuring, between the plurality of electrodes, one or more resistances comprises:
    measuring each of the one or more resistances in one or more sensing zones including a first sensing zone and a second sensing zone, wherein a first resistance of the one or more resistances is measured for the first sensing zone and a second resistance of the one or more resistances is measured for the second sensing zone, the first resistance is measured between two of the plurality of electrodes being exposed by some of a plurality of conduits at some of the plurality of sensor points in the first sensing zone, the second resistance is measured between two of the plurality of electrodes being exposed by some of the plurality of conduits at some of the plurality of sensor points in the second sensing zone.
21. The method of items 19 or 20, wherein detecting the leakage of output comprises:
    determining the leakage of output is present when one or more of the one or more resistances measured is smaller or equal to one of one or more threshold resistances.
22. The method of any of items 19-22, further comprising:
    generating a leakage signal with the monitor device when the leakage of output has been detected.
23. A sensor assembly part for an ostomy system, the sensor assembly part including:
    a first adhesive layer having a distal surface, a proximal surface, and a first plurality of openings, the proximal surface being configured for attachment of the sensor assembly part to the skin surface of a user, and
    an electrode assembly disposed on the distal surface of the first adhesive layer, the electrode assembly including:
        a plurality of electrodes, and
        a masking element between the plurality of electrodes and the first adhesive layer, the masking element having a second plurality of openings aligned with the first plurality of openings of the first adhesive layer to form a plurality of sensor point openings, each of the plurality of sensor point openings exposes a portion of one of the plurality of electrodes to define one of a plurality of sensor points.
24. The sensor assembly part of item 23, wherein a first leakage electrode and a second leakage electrode of the plurality of electrodes are configured to short-circuit through leakage of output when the leakage of output connects the first and second leakage electrodes at a first sensor point and a second sensor point of the plurality of sensor points, one of the plurality of sensor point openings exposing a portion of the first leakage electrode at the first sensor point, and another of the plurality of sensor point openings exposing a portion of the second leakage electrode at the second sensor point.
25. The sensor assembly part of any of items 23-24 comprising one or more sensing zones including a first sensing zone and a second sensing zone, each of the one or more sensing zones includes at least sensing parts of two of the plurality of electrodes.
26. The sensor assembly part of item 25, wherein the plurality of sensor point openings comprises a plurality of primary sensor point openings in the first sensing zone and a plurality of secondary sensor point openings in the second sensing zone, and the plurality of primary sensor point openings comprises one or more primary first sensor point openings exposing a portion of a first leakage electrode of the plurality of electrodes, the plurality of primary sensor point openings comprises one or more primary second sensor point openings exposing a portion of a second leakage electrode of the plurality of electrodes, the plurality of secondary sensor point openings comprises one or more secondary first sensor point openings exposing a portion of a third leakage electrode of the plurality of electrodes, the plurality of secondary sensor point openings comprises one or more secondary second sensor point opening exposing a portion of the second leakage electrode of the plurality of electrodes.
27. The sensor assembly part of any of items 25-26, wherein at least some of the one or more sensing zones are distributed angularly about and/or radially from a stomal opening of the sensor assembly part.
28. The sensor assembly part of any of items 25-27, wherein the first sensing zone is arranged in a first angle space from a center point of a stomal opening of the sensor assembly part and the second sensing zone is arranged in a second angle space from the center point.
29. The sensor assembly part of any of items 25-28, wherein the first sensing zone is arranged in a first radial space from a center point of a stomal opening of the sensor assembly part and the second sensing zone is arranged in a second radial space from the center point.
30. The sensor assembly part of any of items 23-29, wherein the first adhesive layer has a first electrical conductivity, the masking element has a second electrical conductivity, and output has a third electrical conductivity, wherein the second electrical conductivity being lower than the first electrical conductivity, and the third electrical conductivity being higher than the first electrical conductivity.

31. The sensor assembly part of any of items 23-30, wherein the masking element comprises at least one of polymeric and ceramic materials.

32. The sensor assembly part of any of items 23-31, wherein the plurality of electrodes comprises at least one of metallic, ceramic, polymeric, and carbonaceous materials.

33. The sensor assembly part of any of items 23-32, wherein the plurality of electrodes comprises one of silver and carbon.

34. The sensor assembly part of any of items 23-33 being at least one of bendable, flexible, twistable, and stretchable.

35. The sensor assembly part of any of items 23-34 comprising a second adhesive layer coupled distally to the first adhesive layer and the electrode assembly.

36. The sensor assembly part of item 35, wherein the second adhesive layer is at least one of more adhesive to the surface of the subject, more moisture permeable, less moisture-absorbent, and lower in moisture capacity than the first adhesive layer.

37. The sensor assembly part of any of items 23-36 further comprising a release liner releasably attached to the proximal surface of the first adhesive layer, the release liner having a plurality of protrusions configured to extend into the first plurality of openings of the first adhesive layer.

38. The sensor assembly part of any of items 23-37 further comprising a first intermediate element between the first adhesive layer and a plurality of connection parts of the plurality of electrodes.

39. The sensor assembly part of item 38, wherein the first intermediate element is less electrically conductive than the first adhesive layer.

40. The sensor assembly part of any of items 23-39, wherein the electrode assembly further comprises a support layer coupled to the plurality of electrodes.

41. The sensor assembly part of any of items 23-40, wherein the first adhesive layer comprises a hydrocolloid and a polymer matrix.

42. A base plate for an ostomy system, the base plate including:
   a first adhesive layer having a distal surface, a proximal surface, and a first plurality of openings, the proximal surface being configured for attachment of the base plate to the skin surface of a user, and
   an electrode assembly disposed on the distal surface of the first adhesive layer, the electrode assembly including:
      a plurality of electrodes, and
      a masking element between the plurality of electrodes and the first adhesive layer, the masking element having a second plurality of openings aligned with the first plurality of openings of the first adhesive layer to form a plurality of sensor point openings, each of the plurality of sensor point openings exposes a portion of one of the plurality of electrodes to define one of a plurality of sensor points.

43. The base plate of item 42, wherein a first leakage electrode and a leakage second electrode of the plurality of electrodes are configured to short-circuit through leakage of output when the leakage of output connects the first and second leakage electrodes at a first sensor point and a second sensor point of the plurality of sensor points, one of the plurality of sensor point openings exposing a portion of the first leakage electrode at the first sensor point, and another of the plurality of sensor point openings exposing a portion of the second leakage electrode at the second sensor point.

44. The base plate of any of items 42-43 comprising one or more sensing zones including a first sensing zone and a second sensing zone, each of the one or more sensing zones includes at least sensing parts of two of the plurality of electrodes.

45. The base plate of item 44, wherein the plurality of sensor point openings comprises a plurality of primary sensor point openings in the first sensing zone and a plurality of secondary sensor point openings in the second sensing zone, and the plurality of primary sensor point openings comprises one or more primary first sensor point openings exposing a portion of a first leakage electrode of the plurality of electrodes, the plurality of primary sensor point openings comprises one or more primary second sensor point openings exposing a portion of a second leakage electrode of the plurality of electrodes, the plurality of secondary sensor point openings comprises one or more secondary first sensor point openings exposing a portion of a third leakage electrode of the plurality of electrodes, the plurality of secondary sensor point openings comprises one or more secondary second sensor point opening exposing a portion of the second leakage electrode of the plurality of electrodes.

46. The base plate of any of items 44-45, wherein at least some of the one or more sensing zones are distributed angularly about and/or radially from a stomal opening of the base plate.

47. The base plate of any of items 44-46, wherein the first sensing zone is arranged in a first angle space from a center point of a stomal opening of the base plate and the second sensing zone is arranged in a second angle space from the center point.

48. The base plate of any of items 44-47, wherein the first sensing zone is arranged in a first radial space from a center point of a stomal opening of the base plate and the second sensing zone is arranged in a second radial space from the center point.

49. The base plate of any of items 42-48, wherein the first adhesive layer has a first electrical conductivity, the masking element has a second electrical conductivity, and output has a third electrical conductivity, wherein the second electrical conductivity being lower than the first electrical conductivity, and the third electrical conductivity being higher than the first electrical conductivity.

50. The base plate of any of items 42-49, wherein the masking element comprises at least one of polymeric and ceramic materials.

51. The base plate of any of items 42-50, wherein the plurality of electrodes comprises at least one of metallic, ceramic, polymeric, and carbonaceous materials.

52. The base plate of any of items 42-51, wherein the plurality of electrodes comprises one of silver and carbon.

53. The base plate of any of items 42-52 being at least one of bendable, flexible, twistable, and stretchable.

54. The base plate of any of items 42-53 comprising a second adhesive layer coupled distally to the first adhesive layer and the electrode assembly.

55. The base plate of item 54, wherein the second adhesive layer is at least one of more adhesive to the surface of the subject, more moisture permeable, less moisture-absorbent, and lower in moisture capacity than the first adhesive layer.

56. The base plate of any of items 42-55 further comprising a release liner releasably attached to the proximal surface of the first adhesive layer, the release liner having a plurality of protrusions configured to extend into the first plurality of openings of the first adhesive layer.
57. The base plate of any of items 42-56 further comprising a first intermediate element between the first adhesive layer and a plurality of connection parts of the plurality of electrodes.
58. The base plate of item 57, wherein the first intermediate element is less electrically conductive than the first adhesive layer.
59. The base plate of any of items 42-58, wherein the electrode assembly further comprises a support layer coupled to the plurality of electrodes.
60. The base plate of any of items 42-59, wherein the first adhesive layer comprises a hydrocolloid and a polymer matrix.

LIST OF REFERENCES 1 ostomy system
2 ostomy appliance
4 base plate
4' base plate
4" base plate
6 monitor device
8 accessory device
10 server device
12 network
14 coupling member
16 coupling ring
18 stoma-receiving opening
18' stoma-receiving opening
18" stoma-receiving opening
18a central opening of first adhesive layer
18b central opening of second adhesive layer
18c central opening of electrode assembly
19 output
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
207 plurality of protrusions of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
215 monitor interface
216 electrodes of electrode assembly
218 masking element
218A distal surface of masking element
218B proximal surface of masking element
220 electrode configuration
221 connection parts of the electrodes
222 ground electrode
222A ground connection part
222B ground sensing part
224 first electrode
224A first connection part
226 second electrode
226A second connection part
228 third electrode
228A third connection part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
251 one or more of sensing zones
251a first sensing zone
251b second sensing zone
251c third sensing zone
251' one or more of sensing zones
251a' first sensing zone
251b' second sensing zone
251c' third sensing zone
251" one or more of sensing zones
251a" first sensing zone
251b" second sensing zone
251c" third sensing zone
252 fifth terminal opening 253 second plurality of openings of the masking element
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
259 first plurality of openings of first adhesive layer
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
270 plurality of sensor points
270a first sensor point
270b second sensor point
270c third sensor point
271 plurality of sensor point groups
271a primary sensor points
271b secondary sensor points
271c tertiary sensor points
272 plurality of conduits
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
400 central region of the ostomy base plate
400' central region of the ostomy base plate
400" central region of the ostomy base plate
404 outer region of the ostomy base plate
404' outer region of the ostomy base plate
404" outer region of the ostomy base plate
700 sensor assembly part
$R_1$ resistance measured at the first sensing zone
$R_2$ resistance measured at the second sensing zone
$R_{i1}$ first primary resistance value
$R_{i2}$ second primary resistance value
$R_{f1}$ first secondary resistance value
$R_{f2}$ second secondary resistance value
$R_{t1}$ first trigger resistance value
$R_{t2}$ second trigger resistance value
$t_1$ time when short-circuit event occurs at the first sensing zone
$t_2$ time when short-circuit event occurs at the second sensing zone
$t_{t1}$ time when resistance measured in the first sensing zone drops below $R_{t1}$
$t_{t2}$ time when resistance measured in the second sensing zone drops below $R_{t2}$
Δt time-delay The following is claimed:

1. An ostomy system configured to detect leakage of output between a base plate of the ostomy system and a skin surface of a subject, the ostomy system comprising:
the base plate including:
a first adhesive layer having a distal surface, a proximal surface, and a first plurality of openings that extend from the proximal surface to the distal surface, the proximal surface being configured for attachment of the base plate to the skin surface of a user, and
an electrode assembly disposed on the distal surface of the first adhesive layer, the electrode assembly including:
a plurality of electrodes, and
a masking element between the plurality of electrodes and the first adhesive layer, the masking element having a second plurality of openings aligned with the first plurality of openings of the first adhesive layer to form a plurality of sensor point openings, each of the plurality of sensor point openings exposes a portion of one of the plurality of electrodes to define one of a plurality of sensor points;
wherein the plurality of sensor point openings are configured to permit the output to propagate through the sensor point openings and contact the plurality of electrodes; and
a monitor device electrically coupled to the plurality of electrodes of the base plate, the monitor device being configured to (i) measure one or more resistances between the plurality of electrodes through the output and (ii) detect the leakage of output based on one or more resistances.

2. The ostomy system of claim 1, wherein a first leakage electrode and a second leakage electrode of the plurality of electrodes are configured to short-circuit through the leakage of output when the leakage of output connects the first and second leakage electrodes at a first sensor point and a second sensor point of the plurality of sensor points, one of the plurality of sensor point openings exposing a portion of the first leakage electrode at the first sensor point, and another of the plurality of sensor point openings exposing a portion of the second leakage electrode at the second sensor point.

3. The ostomy system of claim 1, configured to detect, using the one or more resistances measured by the monitor device via the plurality of electrodes, the leakage of output propagating from a central region of the base plate towards any direction in a base plane defined by the proximal surface of the first adhesive layer.

4. The ostomy system of claim 1, wherein the base plate comprises one or more sensing zones including a first sensing zone and a second sensing zone, each of the one or more sensing zones includes at least sensing parts of two of the plurality of electrodes.

5. The ostomy system of claim 4, wherein the plurality of sensor point openings comprises a plurality of primary sensor point openings in the first sensing zone and a plurality of secondary sensor point openings in the second sensing zone, and the plurality of primary sensor point openings comprises one or more primary first sensor point openings exposing a portion of a first leakage electrode of the plurality of electrodes, the plurality of primary sensor point openings comprises one or more primary second sensor point openings exposing a portion of a second leakage electrode of the plurality of electrodes, the plurality of secondary sensor point openings comprises one or more secondary first sensor point openings exposing a portion of a third leakage electrode of the plurality of electrodes, the plurality of secondary sensor point openings comprises one or more secondary second sensor point openings exposing a portion of the second leakage electrode of the plurality of electrodes.

6. The ostomy system of claim 4, wherein at least some of the one or more sensing zones are distributed angularly about and/or radially from a stomal opening of the base plate.

7. The ostomy system of claim 4, wherein the first sensing zone is arranged in a first angle space from a center point of a stomal opening of the base plate and the second sensing zone is arranged in a second angle space from the center point.

8. The ostomy system of claim 4, wherein the first sensing zone is arranged in a first radial space from a center point of a stomal opening of the base plate and the second sensing zone is arranged in a second radial space from the center point.

9. The ostomy system of claim 1, wherein the first adhesive layer has a first electrical conductivity, the masking element has a second electrical conductivity, and the leakage of output has a third electrical conductivity, wherein the second electrical conductivity being lower than the first electrical conductivity, and the third electrical conductivity being higher than the first electrical conductivity.

10. The ostomy system of claim 1, wherein the masking element comprises at least one of polymeric and ceramic materials.

11. The ostomy system of claim 1, wherein the plurality of electrodes comprises at least one of metallic, ceramic, polymeric, and carbonaceous materials.

12. The ostomy system of claim 1, wherein the plurality of electrodes comprises one of silver and carbon.

13. The ostomy system of claim 1, wherein the base plate is at least one of bendable, flexible, twistable, and stretchable.

14. The ostomy system of claim 1, wherein the base plate further comprises a second adhesive layer coupled distally to the first adhesive layer and the electrode assembly.

15. The ostomy system of claim 14, wherein the second adhesive layer is at least one of more adhesive to the surface of the subject, more moisture permeable, less moisture-absorbent, and lower in moisture capacity than the first adhesive layer.

16. The ostomy system of claim 1, wherein the base plate further comprises a release liner releasably attached to the proximal surface of the first adhesive layer, the release liner having a plurality of protrusions configured to extend into the first plurality of openings of the first adhesive layer.

17. The ostomy system of claim 1, wherein the base plate further comprises a first intermediate element between the first adhesive layer and a plurality of connection parts of the plurality of electrodes.

18. The ostomy system of claim 17, wherein the first intermediate element is less electrically conductive than the first adhesive layer.

19. The ostomy system of claim 1, wherein the electrode assembly further comprises a support layer coupled to the plurality of electrodes.

20. The ostomy system of claim 1, wherein the first adhesive layer comprises a hydrocolloid and a polymer matrix.

21. The ostomy system of claim 1, wherein the monitor device is configured to generate a leakage signal when the leakage of output is detected in one or more sensing zones.

22. A method of detecting a leakage of output between a base plate of an ostomy system and a skin surface of a subject, the ostomy system including the base plate and a monitor device, the base plate comprising (i) a first adhesive layer having a distal surface, a proximal surface, and a first plurality of openings that extend from the proximal surface to the distal surface, the proximal surface being configured for attachment of the base plate to the skin surface of a user, and (ii) an electrode assembly comprising a plurality of electrodes and a masking element between the plurality of electrodes and the first adhesive layer, the masking element having a second plurality of openings aligned with the first plurality of openings of the first adhesive layer to form a plurality of sensor point openings, each of the plurality of sensor point openings exposes a portion of one of the plurality of electrodes to define one of a plurality of sensor points, wherein the plurality of sensor point openings are configured to permit the output to propagate through the sensor point openings and contact the plurality of electrodes, the monitor device electrically coupled to the plurality of electrodes of the base plate, the method comprising:
measuring, via the plurality of electrodes, one or more resistances, each of the one or more resistances measured between two of the plurality of electrodes through the output; and
detecting the leakage of output based on the measured one or more resistances.

23. The method of claim 22, wherein measuring, between the plurality of electrodes, one or more resistances comprises:
measuring each of the one or more resistances in one or more sensing zones including a first sensing zone and a second sensing zone, wherein a first resistance of the one or more resistances is measured for the first sensing zone and a second resistance of the one or more resistances is measured for the second sensing zone, the first resistance is measured between two of the plurality of electrodes being exposed by some of the plurality of sensor point openings in the first sensing zone, the second resistance is measured between two of the plurality of electrodes being exposed by some of the plurality of sensor point openings in the second sensing zone.

24. The method of claim 22, wherein detecting the leakage of output comprises:
determining that the leakage of output is present when at least one of the one or more resistances measured is smaller or equal to one of one or more threshold resistances.

25. The method of claim 22, further comprising:
generating a leakage signal with the monitor device when the leakage of output has been detected.

26. A base plate for an ostomy system, the base plate comprising:
a first adhesive layer having a distal surface, a proximal surface, and a first plurality of openings that extend from the proximal surface to the distal surface, the proximal surface being configured for attachment of the base plate to a skin surface of a user, and
an electrode assembly disposed on the distal surface of the first adhesive layer, the electrode assembly including:
a plurality of electrodes, and
a masking element arranged between the plurality of electrodes and the first adhesive layer, the masking element having a second plurality of openings aligned with the first plurality of openings of the first adhesive layer, each of the aligned first and second plurality of openings exposes a portion of one of the plurality of electrodes to define one of a plurality of sensor points that are configured to permit output to propagate through the sensor point openings and contact the plurality of electrodes.

\* \* \* \* \*